(12) United States Patent
Collins et al.

(10) Patent No.: US 6,978,517 B2
(45) Date of Patent: Dec. 27, 2005

(54) LOW-PROFILE MOUNTING CLIP FOR PERSONAL DEVICE

(75) Inventors: Sean Collins, Canyon Country, CA (US); Sheldon B. Moberg, Thousand Oaks, CA (US); David S. Kimball, Irvine, CA (US); Timothy J. Payne, Santa Ana, CA (US); Lance E. Shetler, Downey, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 10/719,671

(22) Filed: Nov. 21, 2003

(65) Prior Publication Data

US 2004/0250382 A1 Dec. 16, 2004

Related U.S. Application Data

(63) Continuation-in-part of application No. 10/021,885, filed on Dec. 14, 2001, now Pat. No. 6,665,909.

(51) Int. Cl.[7] ............................................. A45F 5/02
(52) U.S. Cl. ........................................ 24/3.12; 24/3.1
(58) Field of Search ...................... 24/3.1, 3.7, 3.9, 24/3.11–3.12; 224/197, 269, 669, 670, 912, 224/930; 455/90, 351; 379/446, 455

(56) References Cited

U.S. PATENT DOCUMENTS

| | | | |
|---|---|---|---|
| 4,486,918 A | | 12/1984 | Peebles |
| 4,635,836 A | * | 1/1987 | Mooney et al. .............. 224/247 |
| 4,741,074 A | * | 5/1988 | Budano et al. ............... 24/3.11 |
| 4,828,153 A | * | 5/1989 | Guzik et al. ................. 224/242 |
| 4,881,150 A | * | 11/1989 | Oyamada ..................... 361/814 |
| 5,054,170 A | | 10/1991 | Otrusina |
| 5,201,858 A | | 4/1993 | Otrusina |
| 5,261,583 A | * | 11/1993 | Long et al. .................. 224/245 |
| 5,368,427 A | | 11/1994 | Pfaffinger |
| 5,472,317 A | | 12/1995 | Field et al. |
| 5,528,770 A | * | 6/1996 | Castilla et al. .............. 340/7.63 |
| 5,666,700 A | | 9/1997 | Anscher et al. |
| 5,697,538 A | * | 12/1997 | Goldenberg et al. ........ 224/676 |
| 5,906,031 A | | 5/1999 | Jensen |
| 6,032,337 A | * | 3/2000 | Rankin et al. ............... 24/3.12 |
| 6,032,339 A | | 3/2000 | D'Addario |

(Continued)

FOREIGN PATENT DOCUMENTS

EP 0777371 A1 6/1997

(Continued)

*Primary Examiner*—Robert J. Sandy
*Assistant Examiner*—Ruth C. Rodriguez
(74) *Attorney, Agent, or Firm*—Foley & Lardner LLP

(57) ABSTRACT

A low-profile, durable mounting clip for holding personal devices. The mounting clip may have an essentially inverted "L" shaped configuration including a foot portion having engagement elements for attachment to corresponding engagement elements on a housing of a personal device. A leg portion provides for attachment to an undergarment or other suitable article of clothing. A heel portion located between and connecting the leg portion and foot portion allows the foot portion to flexibly and durably retract from the housing. The mounting clip may include a snap tab beam locking mechanism having a barb for interlocking with a bump provided on the housing or a rotatable cam locking mechanism having one or more radial snap tabs having engagement elements for engaging corresponding surfaces on the mounting clip. The mounting clip may have an essentially inverted "C-shaped" configuration including a first foot, a second foot, and a leg portion.

22 Claims, 16 Drawing Sheets

U.S. PATENT DOCUMENTS

| | | | |
|---|---|---|---|
| 6,073,318 A * | 6/2000 | Phillips | 24/3.12 |
| 6,108,944 A | 8/2000 | Savoie | |
| 6,166,695 A | 12/2000 | Witczak et al. | |
| 6,176,401 B1 * | 1/2001 | Lim | 224/196 |
| 6,305,588 B1 | 10/2001 | Michel et al. | |
| 6,311,881 B1 * | 11/2001 | Kamiya | 224/195 |
| 6,470,535 B1 | 10/2002 | Mayne et al. | |
| 6,752,299 B2 * | 6/2004 | Shetler et al. | 224/197 |
| 2002/0002059 A1 | 1/2002 | Johnson | |
| 2003/0141332 A1 * | 7/2003 | Rivera et al. | 224/269 |

FOREIGN PATENT DOCUMENTS

| | | | |
|---|---|---|---|
| JP | 404187102 A * | 7/1992 | |
| JP | 10179233 A | 7/1998 | |
| JP | 2002136322 | 5/2002 | |

* cited by examiner

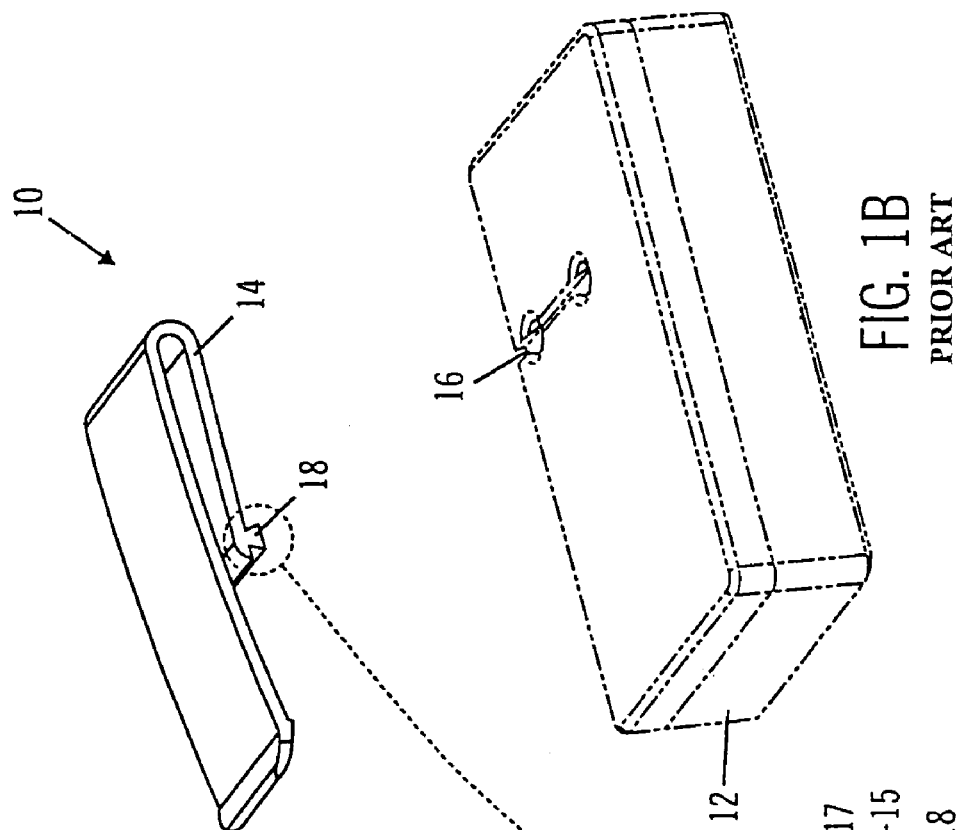
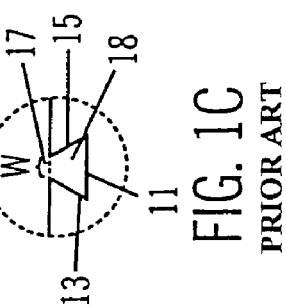
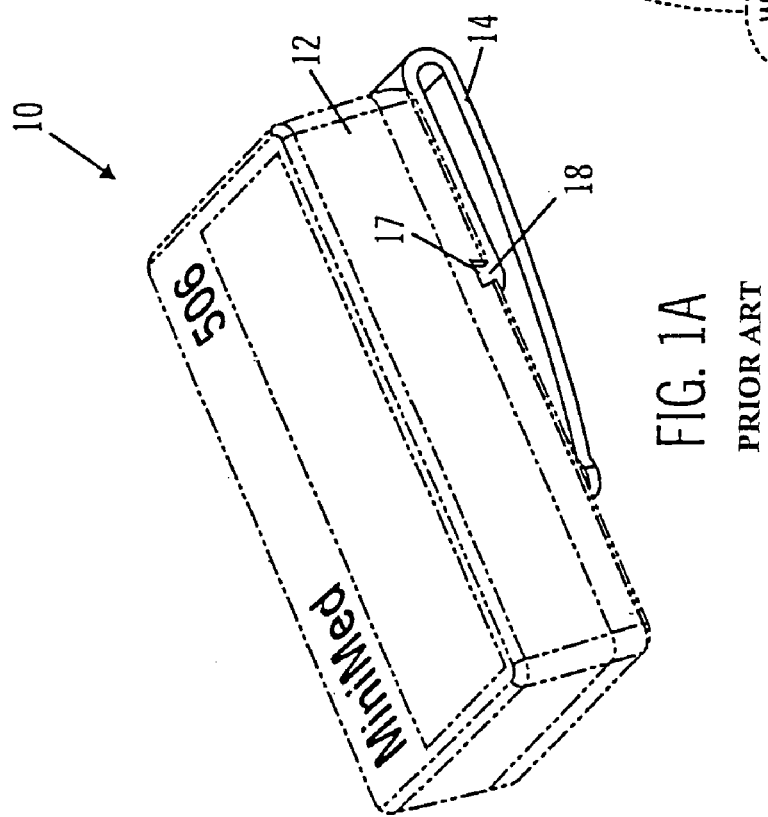
FIG. 1A
PRIOR ART
FIG. 1B
PRIOR ART
FIG. 1C
PRIOR ART

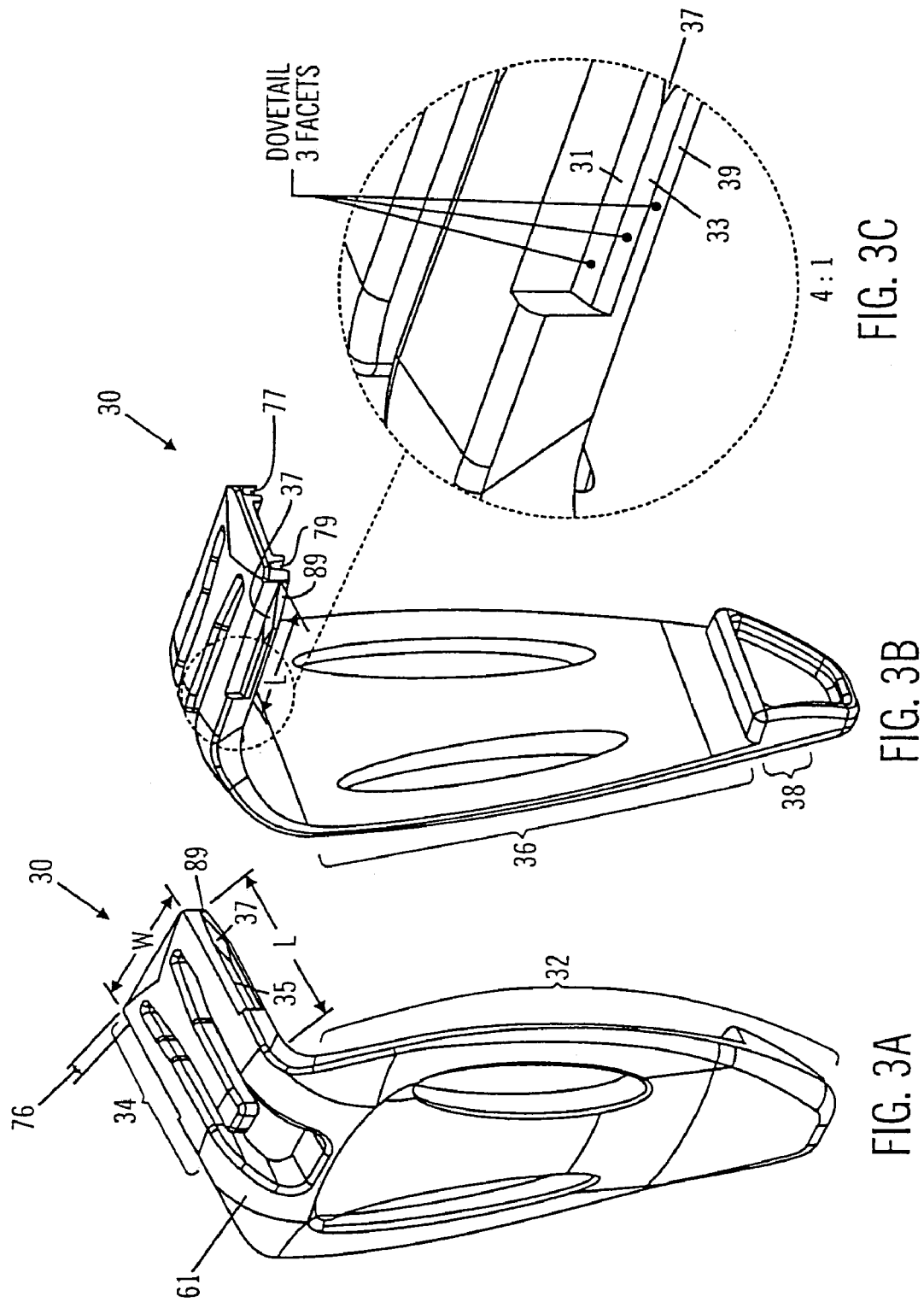

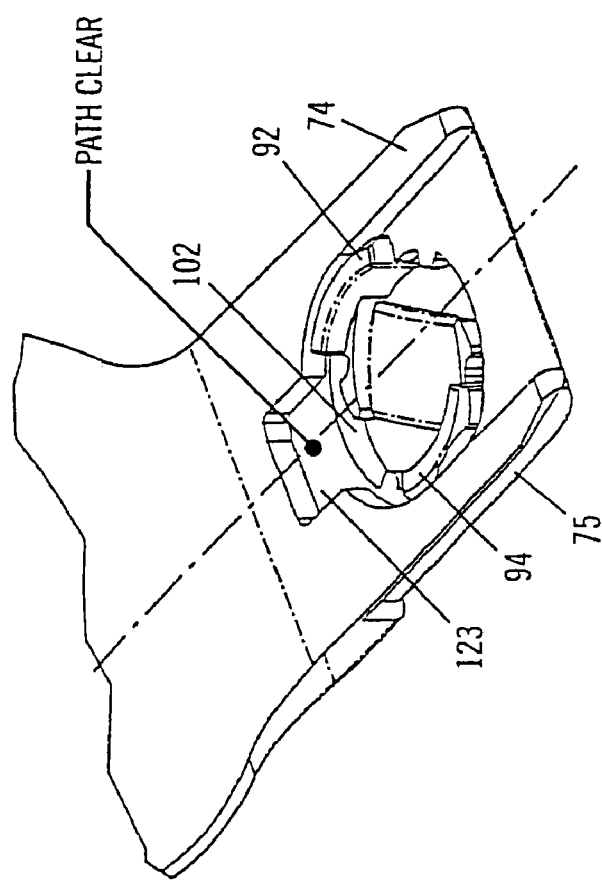
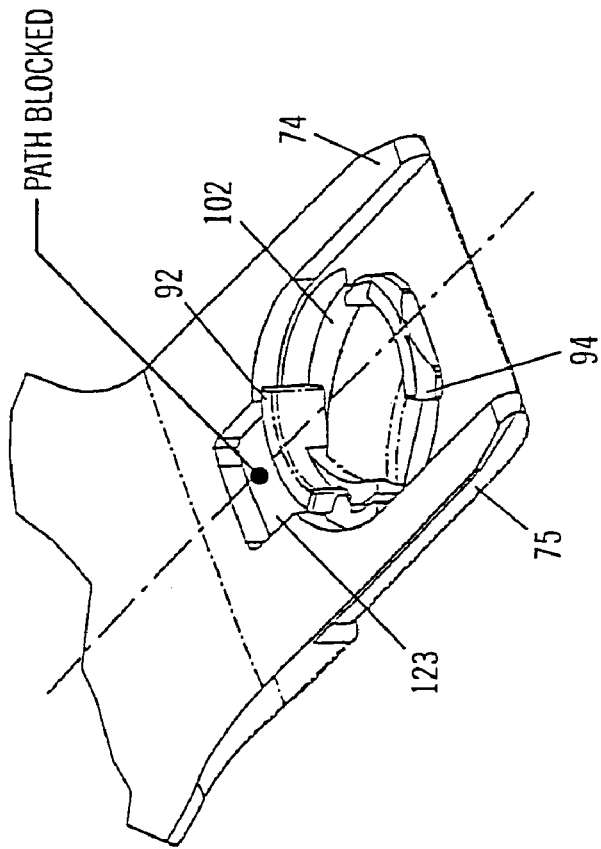
FIG. 4A
FIG. 4B

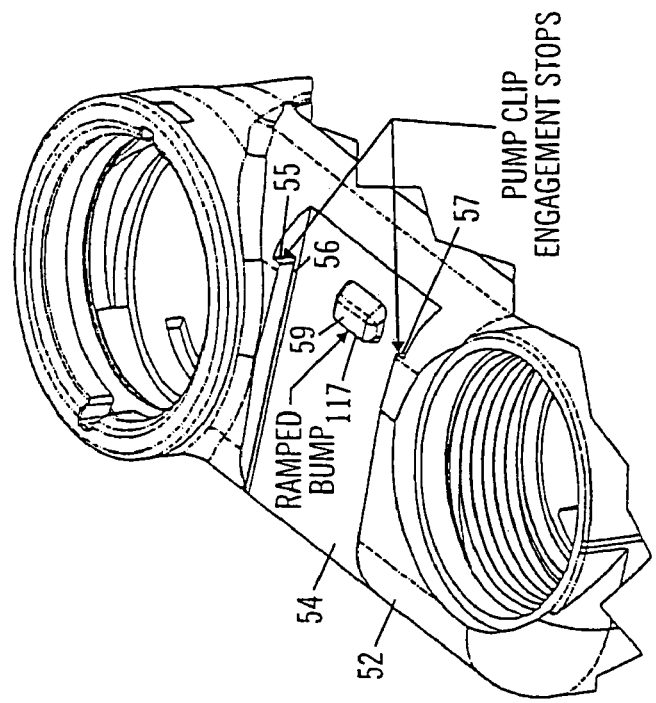
FIG. 5D
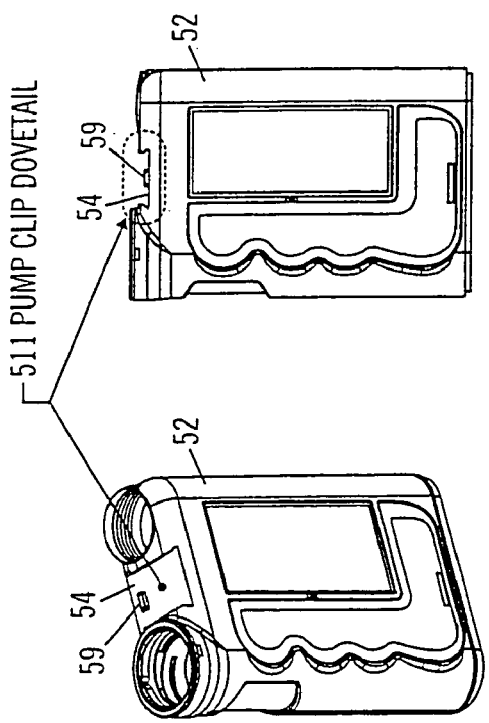
FIG. 5A
FIG. 5B
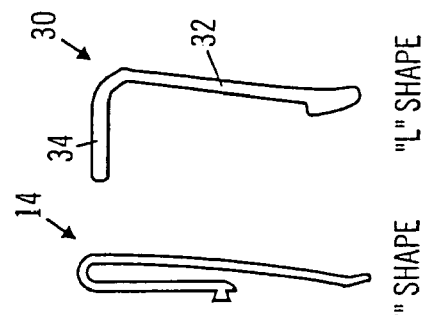
FIG. 5C

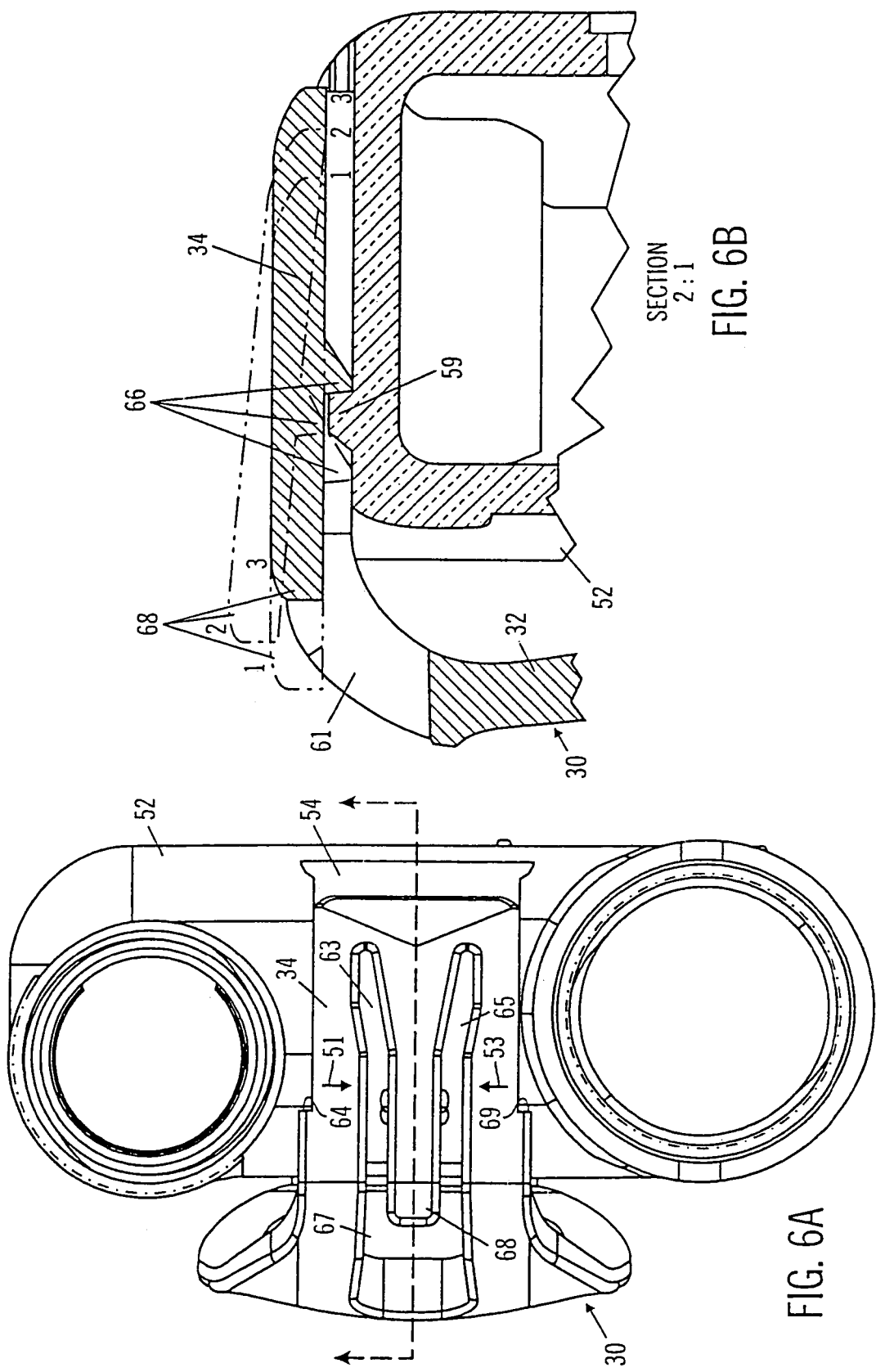

| 230 | Engage second end of clip around second end of personal device. |
|---|---|
| 232 | Guide first end of clip onto first end of personal device. |
| 234 | Ensure clip is secure around personal device. |

FIG. 15

LOW-PROFILE MOUNTING CLIP FOR PERSONAL DEVICE

CROSS REFERENCE TO RELATED APPLICATION

This application is a continuation-in-part of U.S. patent application Ser. No. 10/021,885, entitled "LOW-PROFILE MOUNTING CLIP FOR PERSONAL DEVICE," filed Dec. 14, 2001 now U.S. Pat. No. 6,665,909, assigned to Medtronic MiniMed, Inc., the contents of which are hereby incorporated by reference herein and from which priority is claimed.

BACKGROUND OF THE INVENTION

1. Field of the Invention

The present invention relates, generally, to low-profile durable mounting clips for receiving and supporting personal devices (such as personal electronic devices) and, in particular embodiments, to low-profile mounting clips for inconspicuously holding a personal electronic device such as, but not limited to, an infusion device, a medical monitor or other medical device, in a concealed location by attaching the mounting clip to an article of clothing.

2. Description of Related Art

Various personal devices (such as personal electronic devices) are available that are conveniently adapted to be supported by a mounting clip attached to a user's belt or other article of clothing. Examples of such personal devices include mobile phones, pagers, PDAs, as well as medical devices such as medication infusion pumps and medical monitors. The personal devices are typically adapted for mounting onto a patient's waistband, belt, pocket seam or other suitable clothing item, by using a conventional spring-legged belt clip. In this regard, such mounting clips have typically been designed for connection to the housing of the personal devices (such as personal electronic devices), and for clip-on installation onto the patient's clothing.

FIG. 1A illustrates an example of a spring-legged mounting clip connected to an electronic device. FIG. 1A illustrates an example of a personal medical device, which in this example is a Minimed 506 medication infusion pump. FIG. 1A shows a perspective view of medication infusion pump 10 for delivering or dispensing a prescribed medication to a patient. The medication infusion pump 10 includes a housing 12 enclosing the pump and its associated components. A mounting clip 14 is removably secured to one side of medication infusion pump 10, as shown. The mounting clip 14 shown in FIG. 1A is a unitary part molded in the general shape of an over-bent "U" from a material such as polypropylene. The mounting clip 14 incorporates an elastic living hinge to provide the spring force necessary for expanding and retracting the leg of the U-shaped mounting clip 14 for attachment of the electronic device (such as medication infusion pump 10) to an article of clothing.

FIG. 1B illustrates a perspective view of the medication infusion pump 10 shown in FIG. 1A with the mounting clip 14 separated from the housing 12 in order to show a conventional structure for connecting the mounting clip 14 to the housing 12. As shown in FIG. 1B, included on the housing 12 is a dovetail groove 16 designed for slide-fit reception of a matingly shaped corresponding dovetail boss 18 included on the mounting clip 14. The dovetail groove 16 and mating dovetail boss 18 permit manual slide-on attachment and slide-off removal of mounting clip 14.

FIG. 1C shows dovetail boss 18 in more detail. From FIG. 1C it can be seen that dovetail boss 18 has essentially a wedge shape including a base 11 and two sides 13, 15 extending from the base at essentially symmetrical angles to contact the body of one leg of mounting clip 14. The points of contact between sides 13, 15 of the dovetail boss 18 and mounting clip 14 as they extend transversely across one leg of mounting clip 14 define a flex point 17 of width "w." Flex point 17 thus essentially acts like a pivot pin about the axis of which the mounting clip 14 and housing 12 move in relation to each other. Other mounting clip designs may have a groove and mating boss having a generally rectangular shape where the walls of the boss extend upward at essentially 90 degree angles. In that case, the points of contact between the sides of the rectangular boss and the mounting clip may similarly define a flex point that acts like a pivot pin. In either of these configurations, stresses applied to the mounting clip and/or housing are concentrated at the flex point.

Materials used in conventional mounting clip structures are selected to have a suitable elasticity to provide the spring force required for securing the electronic device (such as medication infusion pump 10) to an article of clothing. In addition, selected materials are employed to avoid heat related deformation and stress relaxation. If such materials are not employed, the initial shape of the mounting clip may be compromised. This is illustrated in FIG. 2, where the mounting clip 14, 14' attached to housing 12 is shown with an initial spring force (shown by solid lines) and a compromised spring force (shown in phantom lines) due to stress relaxation that might occur if suitable materials were not used. Once the spring force has been compromised, secure attachment to an article of clothing may be more difficult to achieve.

Some mounting clips employing the dovetail boss/groove configuration are susceptible to inadvertent separation from the personal device. This may occur, for example, when the mounting clip is designed such that only the friction between the dovetail boss and groove maintains the mounting clip on the personal device. A transverse force contacting the personal device in a direction opposite to that of the direction of slide-on mounting of the dovetail boss into the dovetail groove may cause the personal device to inadvertently partially or fully separate from the mounting clip. Furthermore, a force applied in a direction perpendicular to that of the direction of slide-on mounting of the dovetail boss into the dovetail groove and away from the article of clothing may significantly stress the flex point.

Other mounting clip designs have been used which reduce the chances of separation due to a transverse force as described above. For example, a mounting clip for mounting a medication infusion pump to a patient is described in U.S. Pat. No. 5,472,317. The mounting clip comprises a belt clip with a pair of pivotally interconnected and spring-loaded legs adapted for mounting onto a belt or other item of clothing worn by a patient. One leg of the belt clip includes a dovetail key for slide-fit reception into a mating dovetail boss formed in the housing of a medication infusion pump. A detent button is carried on the belt clip at the distal end of a spring arm for snap-fit reception into a detent seat formed in the pump housing, to lock the pump onto the belt clip. The spring arm is manually accessible to permit fingertip retraction of the detent button from the seat, and permit easy sliding removal of the pump housing from the belt clip. Thus, the locking device may provide protection against separation by a transverse force applied to the housing of the medication infusion pump.

SUMMARY OF THE DISCLOSURE

Embodiments of the present invention relate to low-profile, durable mounting clips for holding personal devices (such as, but not limited to, personal medical devices, personal electronic devices, infusion devices, medical monitors, or the like).

In particular embodiments, a mounting clip having an essentially inverted "L" shaped configuration includes a wide foot portion including engagement elements for attachment to corresponding engagement elements on a housing of a personal device. The mounting clip further includes a leg portion for attachment to an undergarment or other suitable article of clothing that acts as a supporting member. A heel portion located between and connecting the leg portion and foot portion allows the leg portion to flexibly and durably retract away from the housing for attachment to the article of clothing. The inverted "L" shaped configuration allows the leg portion to remain closer to the housing, thus providing a lower profile for ease of attachment to undergarments or other concealed locations on the user's person. At the same time, the inverted "L" shaped configuration and the wider foot provides a stronger and more durable connection to the housing. In the context of a medical device such as, but not limited to, an infusion device or medical monitor, embodiments of the mounting clip allow a user of the device to more confidently and comfortably conceal the device by attaching it to an undergarment or other concealed location on the user's person.

A mounting clip according to an embodiment of the invention includes a foot portion having a dovetail configuration with angled facets arranged in a downwardly and outwardly cascading fashion for engaging corresponding surfaces on a dovetail groove provided on the housing of the personal electronic device (for example, an infusion device or medical monitor). The mating angled facets are configured to allow separation with minimal damage, away from the corresponding and opposing dovetail groove on the housing during an overload condition In particular embodiments, the dovetail configuration further includes a tapered portion at the leading edge of the foot for facilitated attachment of the mounting clip to the housing, as well as providing for extra protection against damage to the mounting clip or housing in a overload condition.

Further embodiments of the mounting clip include voids that allow the solid portions of the foot of the mounting clip to flex inwardly, thus facilitating separation of the foot from the housing with minimal damage. Additional embodiments include channels extending along the foot of the mounting clip in the direction of engagement with the housing that provide additional inward flexibility of the foot of the mounting clip.

In other embodiments, a snap tab beam locking mechanism is provided having a barb for interlocking with a bump provided on the housing to lock the engaged mounting clip onto the housing. In yet other embodiments, a rotatable cam locking mechanism is provided having one or more radial snap tabs having engagement elements for engaging corresponding surfaces on the mounting clip. Rotation of rotatable cam locks the mounting clip onto the housing by blocking movement of the mounting clip in a direction opposite to the direction of engagement.

According to another embodiment of the present invention, a mounting clip for removably attaching a personal device on a supporting member may include a first foot for frictionally attaching the mounting clip to a first portion of the personal device; a second foot for frictionally attaching the mounting clip to a second portion of the personal device; a leg portion for connecting the first foot and the second foot; and a lever hingedly attached to the leg portion. The lever rotates relative to the leg portion for positioning the supporting member between the lever and the leg portion.

BRIEF DESCRIPTION OF THE DRAWINGS

Referring now to the drawings in which like reference numbers represent corresponding parts throughout:

FIG. 1A illustrates an example of a spring-legged mounting clip connected to a medication infusion pump.

FIG. 1B illustrates a perspective view of a medication infusion pump and mounting clip, showing a conventional structure for connecting the mounting clip to the housing of the pump.

FIG. 1C illustrates a dovetail boss.

FIG. 3A shows a perspective view of a mounting clip according to an embodiment of the invention as seen from the back side.

FIG. 3B shows a perspective view of a mounting clip according to an embodiment of the invention as seen from the front side.

FIG. 3C shows a unique dovetail configuration on the foot of a mounting clip according to an embodiment of the invention.

FIG. 4A illustrates a rotatable cam fully attached to a housing and in a locked position, according to an embodiment of the invention.

FIG. 4B illustrates a rotatable cam fully attached to a housing and in an unlocked position, according to an embodiment of the invention.

FIG. 5A illustrates a perspective view of a housing for an infusion device for use with embodiments of the invention.

FIG. 5B illustrates a front view of a housing for an infusion device according to embodiments of the invention.

FIG. 5C illustrates a side view of a generally "inverted L" shaped mounting clip according to an embodiment of the invention in contrast to a side view of a conventional "U" shaped mounting clip.

FIG. 5D illustrates a view of a housing for an infusion device according to embodiments of the invention.

FIG. 6A illustrates a top view of a housing with a mounting clip fully engaged with the housing and locked in place according to an embodiment of the invention.

FIG. 6B illustrates a cross sectional side view of a housing and mounting clip, showing progressive steps in the engagement and locking operation of the foot of the mounting clip with a channel in the housing, according to an embodiment of the invention.

FIG. 15 shows method of a mounting clip with a personal device according to an embodiment of the invention.

DETAILED DESCRIPTION OF PREFERRED EMBODIMENTS

Figure 2:
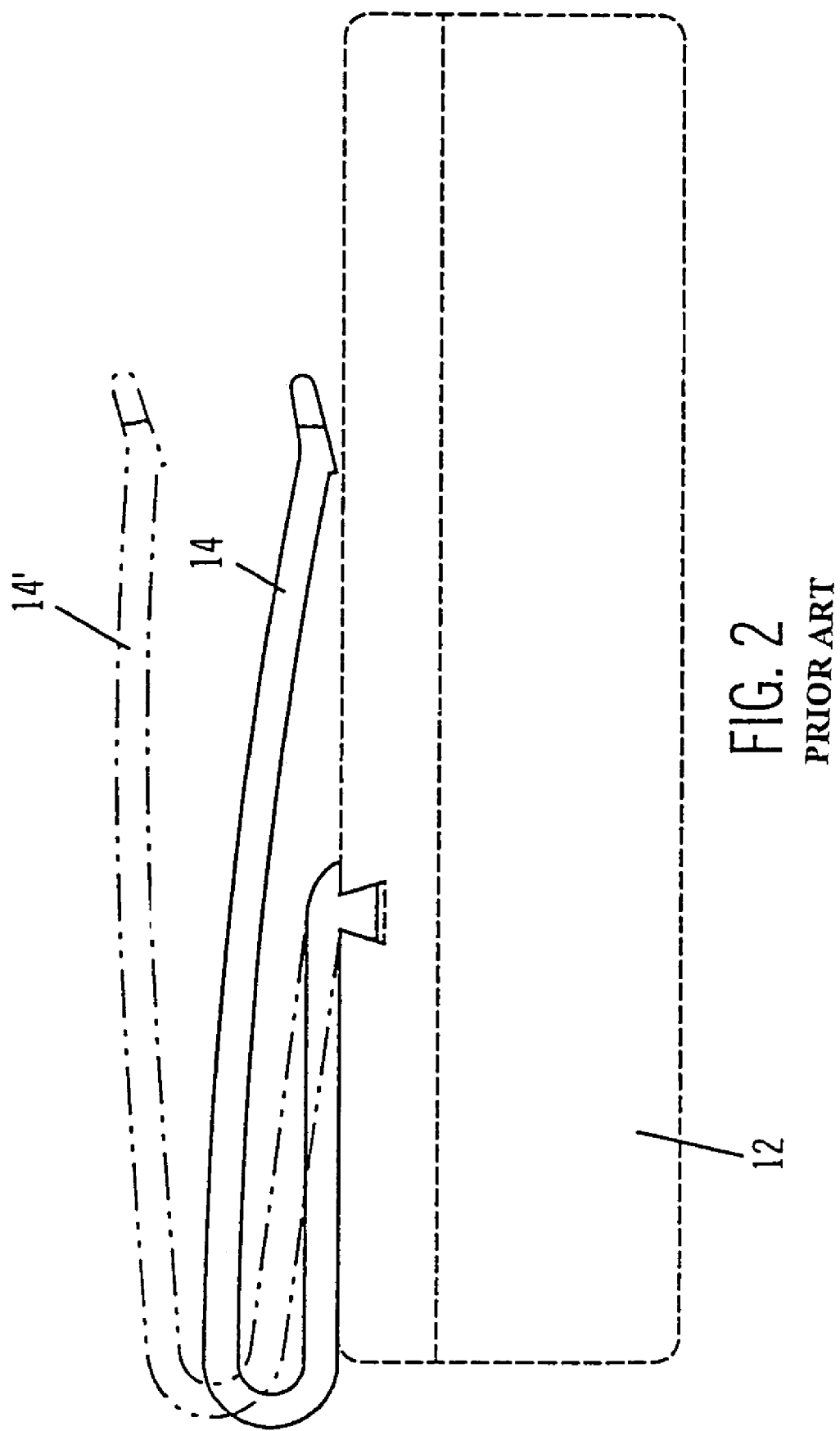
FIG. 2 illustrates a mounting clip attached to a housing and shown with an initial spring force and a compromised spring force.

The following detailed description is of the best presently contemplated mode of implementing the invention. This description is not to be taken in a limiting sense, but is made merely for the purpose of illustrating the general principles of the invention. The scope of the invention is best defined by the appended claims.

As discussed above, embodiments of the present invention relate to low-profile, durable mounting clips for holding personal devices (such as, but not limited to, personal medical devices, personal electronic devices, infusion devices (such as infusion pumps, disposable pumps, constant flow devices, or the like), medical monitors, or the like). In particular embodiments, a mounting clip having an essentially inverted "L" shaped configuration includes a wide foot portion including engagement elements for attachment to corresponding engagement elements on a housing of a personal device. The mounting clip further includes a leg portion for attachment to an undergarment or other suitable article of clothing that acts as a supporting member. A heel portion located between and connecting the leg portion and foot portion allows the foot portion to flexibly and durably retract away from the housing for attachment to the article of clothing. The inverted "L" shaped configuration allows the leg portion to remain closer to the housing, thus providing a lower profile for ease of attachment to undergarments or other concealed locations on the user's person. At the same time, the inverted "L" shaped configuration and the wider foot provides a stronger and more durable connection to the housing. In the context of a medical device such as, but not limited to, an infusion device or medical monitor, embodiments of the mounting clip allow a user of the device to more confidently and comfortably conceal the device by attaching it to an undergarment or other concealed location on the user's person, since the mounting clip has a lower profile than conventional prior art clip designs.

In other embodiments, a snap tab beam locking mechanism is provided having a barb for interlocking with a bump provided on the housing to lock the engaged mounting clip onto the housing. In yet other embodiments, a rotatable cam locking mechanism is provided having one or more radial snap tabs having engagement elements for engaging corresponding surfaces on the mounting clip. Rotation of rotatable cam locks the mounting clip onto the housing by blocking movement of the mounting clip in a direction opposite to the direction of engagement.

A mounting clip according to an embodiment of the present invention is shown in FIGS. 3A and 3B. In FIGS. 3A and 3B, a generally "inverted L" shaped mounting clip 30 (a side view of which is shown in FIG. 5C in contrast to a side view of a "U" shaped mounting clip 14), having a leg portion 32 and a foot portion 34, is shown. FIG. 3A shows a perspective view of mounting clip 30 as seen from the back side, i.e., the side facing away from a housing for a personal device such as, but not limited to, a personal electronic device (not shown) to which mounting clip 30 may be attached. FIG. 3B shows a perspective view of mounting clip 30 as seen from the front side, i.e., the side facing towards a housing for a personal device (not shown) to which mounting clip 30 may be attached.

The foot 34 of mounting clip 30 includes various engagement elements for slideably attaching and securing the mounting clip to a housing of personal device (such as, but not limited to, personal medical devices, personal electronic devices, infusion devices, medical monitors, or the like) having corresponding engagement elements designed to slideably receive and secure the foot 34 of mounting clip 30. The leg 32 of mounting clip 30 is designed such that, when the mounting clip 30 is attached and secured to a housing, at least a first portion of the leg 32 facing the housing, for example portion 36 shown in FIG. 3B, is spaced a distance apart from the housing. Thus, a defined space is provided between the leg 32 and the housing for receiving a strap, belt, or other article of clothing used to support the mounting clip 30. The leg 32 of mounting clip 30 is further designed such that, when attached to a housing, at least a second portion of the leg 32, for example portion 38 shown in FIG. 3B, retractably abuts a portion of the housing. Thus, the strap, belt, or other article of clothing used to support the mounting clip 30 is enclosed within the defined space defined by the heel 61 and the portion 38.

In one embodiment, mounting clip 30 may be a unitary inverted "L"-shaped part molded from a suitably rigid material such as, but not limited to, polycarbonate. The inverted "L" shape and the more rigid material are employed to provide additional strength to mounting clip 30. The foot 34 of mounting clip 30 may have a length and width (shown as "L" and "W," respectively in FIG. 3A) that provide added strength at a heel 61 (best shown in FIG. 6B) in order to reduce the possibility of compromised spring force due to stress relaxation of the mounting clip 30. Thus, the engaged portion (i.e. foot 34) remains durably secured and substantially stationary relative to the housing. At the same time, the mounting clip 30 has elasticity such that the unengaged portion of mounting clip 30 (i.e., leg 32) is allowed to be retractably pulled back away from the housing for attachment to an article of clothing. Thus, a spring force is provided for mounting clip 30 while avoiding the drawbacks of clip designs incorporating a living spring, such as stress relaxation of the spring force.

In addition, in one embodiment, mounting clip 30 and the housing are designed such that the foot 34 of the "L" engages a top portion of the housing in a manner that allows the leg 32 to remain closer to the housing, thus reducing the overall thickness of the mounting clip 30/housing combination. Thus, the mounting clip 30/housing combination can have a lower profile and may be more discretely attached by the user to an undergarment or other concealed clothing item than would be possible with conventional prior art clip designs.

The abutting portion 38 of mounting clip 30 may be manually pulled back from the housing for attachment to the article of clothing by, for example, fingertip retraction. Alternatively, the abutting portion 38 may be separated from the housing by sliding a strap, belt, or other article of clothing against the point of contact between the abutting portion 38 and the housing. The strap, belt, or other article of clothing, thus separates and passes between the abutting portion 38 and the housing. When the strap, belt, or other article of clothing clears the abutting portion 38 and enters the defined space, the abutting portion 38 again returns to its abutting position to act as a barrier against inadvertent detachment of the mounting clip 30 from the article of clothing.

In one embodiment, the mounting clip 30 is designed to provide improved protection against inadvertent detachment due to forces exerted transverse to the flex point or heel 61 of mounting clip 30. Further embodiments include additional features on foot 34 of mounting clip 30 that reduce the risk of damage to the mounting clip 30 from an overload condition at the heel 61 due to forces exerted both transverse and perpendicular to mounting clip 30. In addition, in further embodiments, mounting clip 30 may provide a locking feature for locking mounting clip 30 to a housing of a personal device (such as, but not limited to, personal medical devices, personal electronic devices, infusion devices, medical monitors, or the like).

Referring again to FIGS. 3A and 3B, one embodiment of engagement elements for slideably attaching and securing the mounting clip to a housing of a personal device having corresponding engagement elements designed to slideably receive and secure the mounting clip 30 will be described.

In some embodiments, foot 34 includes a multi-faceted dovetail configuration 35 formed along at least a portion of its sides as best shown in FIGS. 3B and 3C. FIGS. 3B and 3C show the faceted dovetail configuration 35 extending for length L' on one side of foot 34. Other embodiments of the multi-faceted dovetail configuration may have other suitable lengths. The other side of foot 34 includes a substantially identical and symmetrical dovetail configuration (not shown). FIG. 3C shows the dovetail configuration 35 of FIG. 3B in more detail. Dovetail configuration 35 may include one or more angled facets (three angled facets 31, 33, 39 are shown in FIG. 3C) arranged in an outwardly and downwardly cascading fashion. In one embodiment, the angled facets are designed such that the uppermost facet in the cascade (facet 31 in FIG. 3C) slopes outwardly and downwardly at a defined angle. The middle facet in the cascade (facet 33 in FIG. 3C) slopes outwardly and downwardly at a defined angle that is steeper than the angle of the uppermost facet. The lowermost facet in the cascade (facet 39 in FIG. 3C) slopes outwardly and downwardly at a defined angle that is steeper than both the angles of both the uppermost and middle facets. The angled facets 31, 33, 39 are designed to slideably engage corresponding engagement elements on a housing. In further embodiments, the dovetail configuration 35 may include a faceted portion 37 on both sides of the leading edge of the dovetail configuration 35 (i.e., the "toe" portion of foot 34) that first engages the corresponding engagement element of the housing. Faceted portions 37 facilitate the initial engagement between the mounting clip 30 and the engagement elements of the housing.

One embodiment of a housing having corresponding engagement elements for receiving the foot 34 of mounting clip 30 is shown in FIGS. 5A and 5B. FIGS. 5A and 5B show perspective and front views, respectively, of a housing 52 for an infusion device. Housing 52 includes on its top surface a channel 54 designed to have a size and shape suitable for receiving the foot 34 of mounting clip 30. In one embodiment, channel 54 is integrally formed with housing 52, for example by a molding process. Other embodiments may form channel 54 by other suitable processes.

FIG. 5D shows a perspective view of housing 52 with its back side to the right, showing channel 54 in more detail. In FIG. 5D, a dovetail groove 56 is shown on one side of channel 54. Channel 54 includes a substantially identical and symmetrical dovetail groove (not shown) on its other side. The dovetail grooves 56 are designed to have a size and shape for slideably receiving the dovetail configurations 35 located on the sides of mounting clip 30 such that the surfaces of the angled facets 31, 33 and 39 are mated to corresponding surfaces (not shown) of the dovetail grooves 56.

In a further embodiment, channel 54 further includes a ramped snap tab bump 59 (best shown in FIG. 5D) which cooperates with a corresponding snap tab barb 66 (best shown in FIG. 6B) located on snap tab beam 68 (best shown in FIG. 6A) to lock mounting clip 30 to housing 52 when fully engaged. The operation of the snap tab beam 68 locking mechanism is described in relation to FIGS. 6A and 6B. FIG. 6A shows a top view of housing 52 with mounting clip 30 fully engaged in channel 54 and locked in place. FIG. 6B shows a cross sectional side view of housing 52 and mounting clip 30 showing progressive steps in the engagement and locking operation of foot 34 with channel 54.

At step 1, as shown in FIG. 6B, the snap tab barb 66 on snap tab beam 68 (shown by phantom lines) approaches snap tab bump 59 as the foot 34 of mounting clip 30 begins to engage channel 54. At step 2, the snap tab barb 66 on snap tab beam 68 (shown by phantom lines) begins to ride over the snap tab bump 59 as the foot 34 of mounting clip 30 further engages channel 54. The snap tab beam 68 is designed such that it elastically flexes in an upward direction to allow the snap tab barb 66 to ride up and over snap tab bump 59. At step 3, the snap tab barb 66 on snap tab beam 68 (shown by solid lines) has overridden the snap tab bump 59 and snapped back to the surface of channel 54. At this point, the foot 34 of mounting clip 30 is fully engaged with channel 54 and locked in place. In one embodiment, channel 54 further includes engagement stops 55 and 57 (FIG. 5D) for abutting against corresponding surfaces 64 and 69 of foot 34 (best shown in FIG. 6A) when full engagement of mounting clip 30 with channel 54 is achieved. The mounting clip 30 may be removed from the housing by lifting up the snap tab beam 68 until the snap tab barb 66 clears the snap tab bump 59 and the mounting clip 30 may be slideably removed in a direction opposite to that of engagement.

As discussed above, in one embodiment, the surfaces of the angled facets 31, 33, and 39 of dovetail configurations 35 are mated to corresponding surfaces of the dovetail grooves 56 when the mounting clip 30 is fully engaged to the housing 52. It is possible that a sufficient force could be exerted on the mounting clip 30 and/or housing 52 to cause an overload condition. An overload condition may result, for example, when a force in a direction other than the direction of engagement between the foot 34 and channel 54 causes the angled facets 31, 33, and 39 to be pushed up against the corresponding surfaces of the dovetail grooves 56 until a separation of the foot 34 from channel 54 occurs, thus causing mounting clip 30 to inadvertently separate from housing 52. In one embodiment, the angled facets 31, 33, and 39 of dovetail configurations 35 are designed in a downwardly and outwardly cascading fashion such that they may elastically deform, slide from facet to facet along the corresponding and opposing surfaces of the housing, and separate from the housing 52 with minimal damage to either the mounting clip 30 or the housing 52. In some embodiments, mounting clip 30 and/or housing 52 may include a material such as, but not limited to, polytetrafluoroethylene and aramid fibers, in order to add more lubricity and strength to dovetail configuration 35. The added lubricity allows the angled facets to more easily slide from one facet surface to the next and with reduced resistance to slide along a corresponding and opposing surface of the housing with reduced friction.

In further embodiments, foot 34 of mounting clip 30 may include voids 63, 65, and 67 (best shown in FIG. 6A) formed in the solid material of foot 34 by, for example, a molding process. In the event of an overload condition as described above, voids 63, 65, and 67 allow the solid portions of foot 34 to flex inwardly, as shown by arrows 51 and 53. This inward flexibility allows the engagement elements along the sides of foot 34, for example angled facets 31, 33, and 39 of dovetail configurations 35, to separate with minimal damage away from the corresponding and opposing surface of the housing, for example dovetail grooves 56, during an overload condition. Thus, the engagement elements separate and the mounting clip 30 is free to separate from the housing with minimal damage to either.

In still further embodiments, foot 34 may include channels 77, 79 (best shown in FIG. 3B) that extend along foot 34 in the direction of engagement with housing 52 for a defined length. In one embodiment, channels 77, 79 extend along the bottom of foot 34. Channels 77, 79 provide additional inward flexibility that allows the engagement elements of foot 34 (for example angled facets 31, 33, 39) to separate from corresponding engagement elements (for example angled surfaces of the dovetail grooves 56) with minimal damage under an overload condition. When an overload condition occurs, the engagement elements located along the sides of foot 34 are allowed, due to channels 77, 79 to flex inwardly away from corresponding engagement elements on the housing 52.

In the embodiment of mounting clip 30 shown in FIG. 3A, voids 63, 65, and 67 do not extend completely to the toe of foot 34. Instead a solid portion 76 of foot 34 exists at the toe. Thus, there is reduced inward flexibility at solid portion 76. In this embodiment, tapered portions 89 (FIG. 3B) may reduce binding within the dovetail connection and facilitate disengagement of solid portion 76 from the corresponding and opposing surface of the housing by providing a taper along both sides of the foot 34 at the solid portion 76 of the toe.

In various embodiments described above, an integrally formed snap tab beam/barb configuration is employed for locking the fully engaged mounting clip to the housing. Such a configuration has advantages. For example, it requires less material in the foot portion due to the voids therein and may provide improved flexibility to the leg portion of the mounting clip.

Figure 7C:
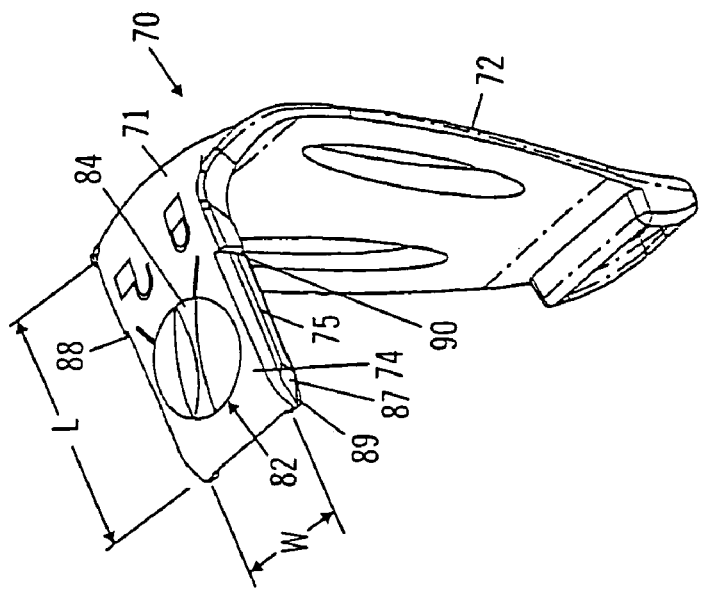
FIG. 7C illustrates a perspective view of a mounting clip having a rotatable cam locking mechanism, according to an embodiment of the invention.
Figure 7B:
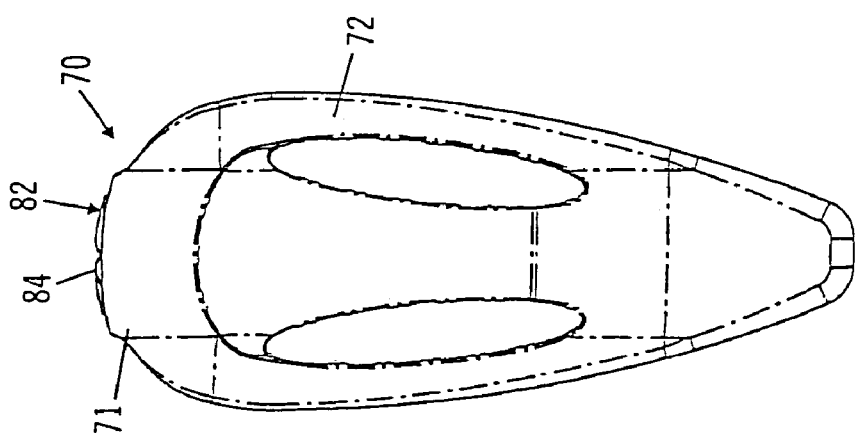
FIG. 7B illustrates a back view of a mounting clip having a rotatable cam locking mechanism, according to an embodiment of the invention.
Figure 7A:
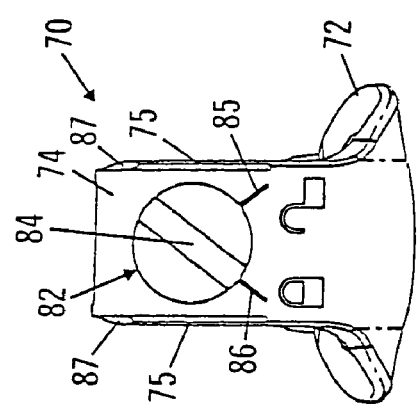
FIG. 7A illustrates a top view of a mounting clip having a rotatable cam locking mechanism, according to an embodiment of the invention.

A mounting clip having another type of locking mechanism is shown in the embodiment of FIGS. 7A, 7B and 7C. FIGS. 7A, 7B and 7C show top, back and perspective views, respectively, of mounting clip 70. Embodiments of mounting clip 70 replace the snap tab beam/barb locking configuration with a rotatable cam 82 locking feature for locking the mounting clip 70 to a housing 52. As described and illustrated above, the snap tab beam/barb configuration provided a barb 66 located on a snap tab beam 68 for riding up and over a bump 59 located on housing 52 for locking the mounting clip to the housing 52. In contrast, embodiments of the rotatable cam 82 locking feature include one or more radial snap tabs 92, 94 positioned on the rotatable cam 82. The one or more radial snap tabs 92, 94 are positioned such that when rotatable cam 82 is in the unlocked position 85, a clear path is provided for slideably attaching the mounting clip 70 to housing 52 (best shown in FIG. 4B). When rotatable cam 82 is fully attached to housing 52 and is rotated to the locked position 86, at least one of the radial snap tabs 92, 94 is positioned such that it aligns, in an essentially parallel manner, with the flat surface of a bump located on the housing. Thus, the mounting clip 70 is blocked by the bump from moving in a direction opposite to that of the direction of attachment (best shown in FIG. 4A). Therefore, a more convenient method of locking the mounting clip 70 to the housing is provided. The rotatable cam 82 locking feature is also advantageous in that it adds more durability to the mounting clip 70 because more material is used in the foot 74, increasing its rigidity.

The rotatable cam 82 may, in one embodiment, be formed, for example by molding, separately from the remainder of the mounting clip. The rotatable cam 82 may subsequently be inserted into an opening 102 formed, for example by molding, in the foot 74 of the mounting clip 70 and designed to have a size and shape for receiving the rotatable cam 82. The opening 102 may include, along its sides, one or more engagement stops for abutting against corresponding surfaces formed on the inserted rotatable cam 82. In one embodiment, the engagement stops are opposing, symmetrical mechanical stops 105, 107 that limit the rotation of the rotatable cam 82 to 75 degrees between unlocked and locked positions. Other embodiments may employ other engagement stop configurations.

In further embodiments, the rotatable cam 82 may include a notch 84 for insertion of a coin, key, paper clip, credit card or other suitable tool that may be used to rotate the rotatable cam 82 between locked and unlocked positions. In still other embodiments, the rotatable cam 82 may include dual opposing snap tab features that provide audible and tactile indicators to indicate to a user that the rotatable cam 82 is in a locked position. In one embodiment, visual indicators of the same may be included on the mounting clip and/or housing as well.

In another embodiment, one or more of the dimensions of the rotatable cam 82 and opening 102 are selected to result in a frictional fit between the rotatable cam 82 and the opening. The frictional fit is sufficient to maintain the rotatable cam 82 firmly in intermediate positions between the unlocked and locked positions.

FIGS. 7A, 7B and 7C show top, back and perspective views, respectively, of mounting clip 70, having a leg portion 72, a foot portion 74 and a heel portion 71. In one embodiment, mounting clip 70 may have a generally inverted "L"-shape and may include two or more parts molded from a suitably rigid material such as, but not limited to, a polycarbonate. As in the previous embodiment discussed above, the inverted "L" shape and the more rigid material are employed to provide additional strength to mounting clip 70. The foot 74 of mounting clip 70 may have a length and width (shown as "L" and "W," respectively in FIG. 7C) that provide added strength at a heel 71 in order to reduce the possibility of compromised spring force due to stress relaxation of the mounting clip 70. Furthermore, as discussed above, added durability may be provided by the increased material used in foot 74 of mounting clip 70 as opposed to foot 34 of mounting clip 30. Thus, the engaged portion (i.e. foot 74) remains durably secured and substantially stationary relative to the housing 52 (shown in FIGS. 5A, 5B and 5D). At the same time, the mounting clip 70 has elasticity such that the unengaged portion of mounting clip 70 (i.e., leg 72) is allowed to be retractably pulled back away from the housing for attachment to an article of clothing. Thus, a spring force is provided for mounting clip 70 while avoiding the drawbacks of clip designs incorporating a living spring, such as stress relaxation of the spring force.

As can be seen from FIGS. 7A and 7C, embodiments of mounting clip 70 may additionally include a dovetail configuration 75 along the sides of foot 74 having one or more angled facets that are designed to slideably engage corresponding engagement elements on housing 52. In further embodiments, the dovetail configuration 75 may include faceted portions 87 on both sides of the toe of the dovetail configuration 75. The details and advantages of the dovetail configuration 75 and faceted portions 87 have been discussed above in relation to mounting clip 30. Further embodiments may include engagement stops 88 and 90 for abutting against corresponding surfaces 55 and 57 (FIG. 5D) of housing 52 when full engagement of mounting clip 70 with channel 54 is achieved. In still further embodiments, mounting clip 70 and/or housing 52 may include a material such as, but not limited to, polytetrafluorethylene and aramid fibers, to add more lubricity and strength to dovetail configuration 75. The added lubricity has the advantages discussed above in relation to mounting clip 30.

Figure 8A:
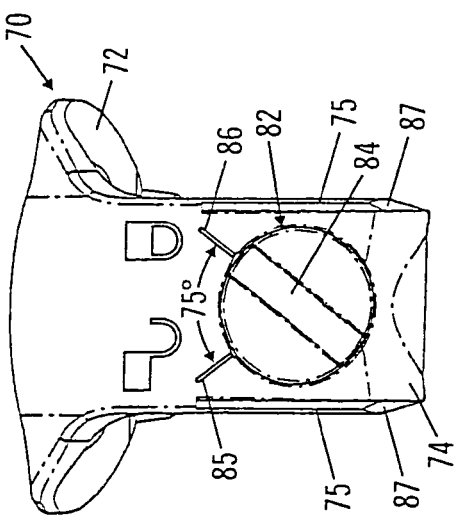
FIG. 8A illustrates a top view of a rotatable cam locking mechanism in a locked position, according to an embodiment of the invention.
Figure 8B:
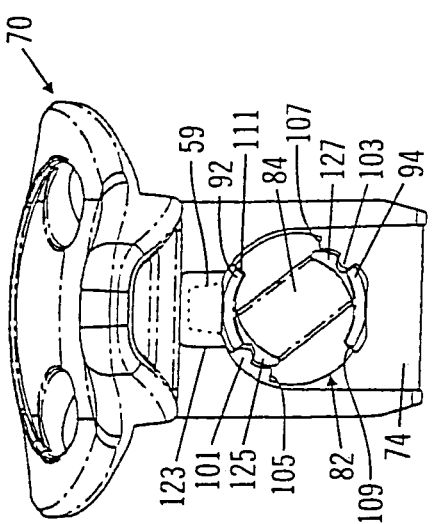
FIG. 8B illustrates a bottom view of a rotatable cam locking mechanism in a locked position, according to an embodiment of the invention.
Figure 8C:
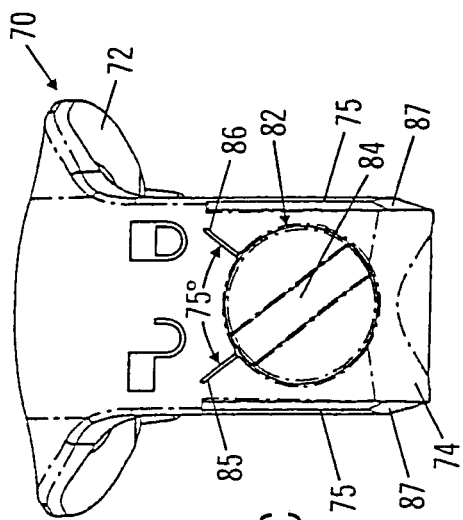
FIG. 8C illustrates a top view of a rotatable cam locking mechanism in an unlocked position, according to an embodiment of the invention.
Figure 8D:
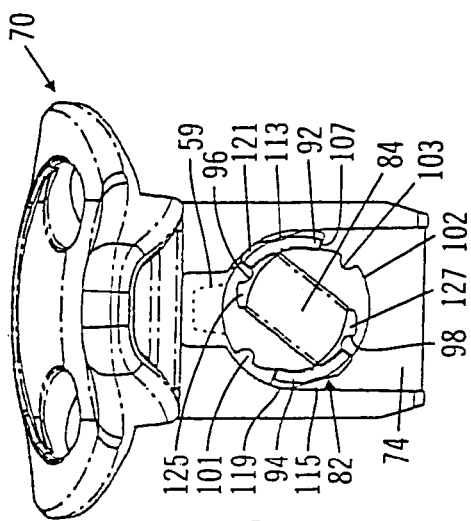
FIG. 8D illustrates a bottom view of a rotatable cam locking mechanism in an unlocked position, according to an embodiment of the invention.

FIGS. 8A and 8B show top and bottom views, respectively, of rotatable cam 82 in the locked position. FIGS. 8C and 8D show top and bottom views, respectively, of rotatable cam 82 in the unlocked position. As discussed above, in one embodiment, rotatable cam 82 may be rotated, for example by a coin inserted in notch 84, between an unlocked position 85 and a locked position 86. In on embodiment, the rotational span between unlocked position 85 and a locked position 86 may be approximately 75 degrees (as shown in FIGS. 8A and 8B). Other embodiments may employ different rotational spans.

In one embodiment, rotatable cam 82 includes two essentially symmetrical radial snap tabs 92, 94 positioned on opposing sides of the rotatable cam 82. The radial snap tabs 92, 94 include integrally formed and essentially symmetrical indentations 96, 98 designed for snap-fit reception of matingly shaped corresponding buttons 101, 103 integrally formed on the sides of opening 102. Further embodiments include engagement stops 105, 107 (best shown in FIG. 8B) for abutting against corresponding surfaces 109, 111 on radial snap tabs 92, 94 when rotatable cam 82 is in the unlocked position 85 (as shown in FIG. 8D).

In one embodiment, radial snap tabs 92, 94 further include on their outer walls flat surfaces 113, 115 (best shown in FIG. 8D) designed to abut a corresponding flat surface 117 on bump 59 (FIG. 5D). Indentation 123 is integrally formed in foot 74 to provide clearance for bump 59 when the mounting clip 70 is fully engaged with housing 52. Thus, when the mounting clip 70 is fully engaged with housing 52 and rotatable cam 82 is in the locked position 86, bump 59 (as shown by phantom lines) will be positioned within indentation 123 with its flat surface 117 abutting flat surface 113 on radial snap tab 92.

Although, according to one embodiment, for a particular orientation of rotatable cam 82, only one of radial snap tabs 92, 94 can contact bump 59 when in the locked position (radial snap tab 92 as shown in FIGS. 8B and 8D), rotatable cam 82 is designed to be symmetrical such that, when inserted in opening 102 during the manufacturing process, it does not require a specific orientation. Thus, however the rotatable cam 82 is oriented when inserted in opening 102 during manufacturing, a flat side of radial snap tabs 92, 94 will abut flat surface 117 on bump 59 when in the locked position 86.

Further embodiments of radial snap tabs 92, 94 may include barbs 119, 121 or similar structures integrally formed with the radial snap tabs 92, 94 that facilitate retention of rotatable cam 82 within opening 102 by overhanging the outside diameter of opening 102 and thus reduce the chances of separation of rotatable cam 82 from mounting clip 70.

In one embodiment, the locking mechanism of the rotatable cam 82 operates in the following manner. As rotatable cam 82 is rotated from the unlocked position 85 towards the locked position 86, a leading edge of radial snap tab 92 encounters the flat surface 117 of bump 59. As rotatable cam 82 continues to rotate towards the locked position 86, radial snap tab 92 begins to elastically bend or compress back as it continues to encounter bump 59. Within a short rotational span after the leading edge of radial snap tab 92 encounters the flat surface 117 of bump 59, the leading edges 125, 127 of indentations 96, 98 begin to contact matingly shaped corresponding buttons 101, 103 and similarly begin to bend or compress back, thus facilitating the angular displacement of radial snap tab 92 as a whole.

As rotatable cam 82 continues to rotate towards the locked position 86, an over center, cam action is created by the compressed material. The over center, cam action facilitates the completion of the rotation and flat surface 113 of radial snap tab 92 aligns, in an essentially parallel manner, with the flat surface 117 of bump 59. Also, substantially simultaneously, as the flat surface of radial snap tab 92 aligns with the flat surface 117 of bump 59, indentations 96, 98 align with matingly shaped corresponding buttons 101, 103. Thus, the radial snap tab 92 and indentations 96, 98 snap fit to the flat surface 117 of bump 59 and matingly shaped corresponding buttons 101, 103, respectively. Thus, the locked position 86 is achieved.

Further embodiments of mounting clip 70 are designed to provide the user with audible, visible and/or tactile indicators to indicate that rotatable cam 82 is in the locked position 86. In some embodiments, the engagement elements of the rotatable cam 82, for example indentations 96, 98 of radial snap tab 92, are designed to produce a sound such as, but not limited to, an audible click or snap when achieving a snap fit with the corresponding engagement elements located on foot 74, for example buttons 101, 103. In other embodiments, the engagement elements of the rotatable cam 82 are designed to produce, in the alternative or in addition to the audible click or snap, a tactile feel indicating a locked position 86. Yet other embodiments are designed to produce tactile and/or audible indicators indicating that the rotatable cam 82 is disengaging from the locked position 86. Still other embodiments may include visual indicators of the unlocked position 85 and locked position 86, such as, but not limited to, silk screened text, pictures, or other indicia indicating the unlocked and locked positions.

In one embodiment, to facilitate manufacturing of mounting clip 70, the design of the rotatable cam 82 incorporates a chamfer, taper or similar edge configuration along the bottom edges of rotatable cam 82 and/or along the top edges of opening 102 to assist in the snap fit assembly of the rotatable cam 82 to the foot 74 of mounting clip 70. Thus, the rotatable cam 82 may, for example, be seated and press fit into opening 102. As the rotatable cam 82 is press fit into opening 102, the radial snap tabs 92, 94 elastically bend or compress inward and allow rotatable cam 82 to seat in opening 102, whereupon the radial snap tabs 92, 94 return to their original position. In another embodiment, one or more of the dimensions of the rotatable cam 82 and opening are selected to result in a frictional fit between the rotatable cam 82 and the opening sufficient to maintain the rotatable cam 82 firmly in intermediate positions between the unlocked and locked positions. In further embodiments, barbs 119, 121 facilitate retention of rotatable cam 82 within opening 102, once seated, by overhanging the outside diameter of opening 102, thus reducing the chances of separation of rotatable cam 82 from mounting clip 70 due to flexing of foot 74. As discussed above, in one embodiment, rotatable cam 82 is designed to be symmetrical such that, when inserted in opening 102 during the manufacturing process, it does not require a specific orientation.

Figure 9:
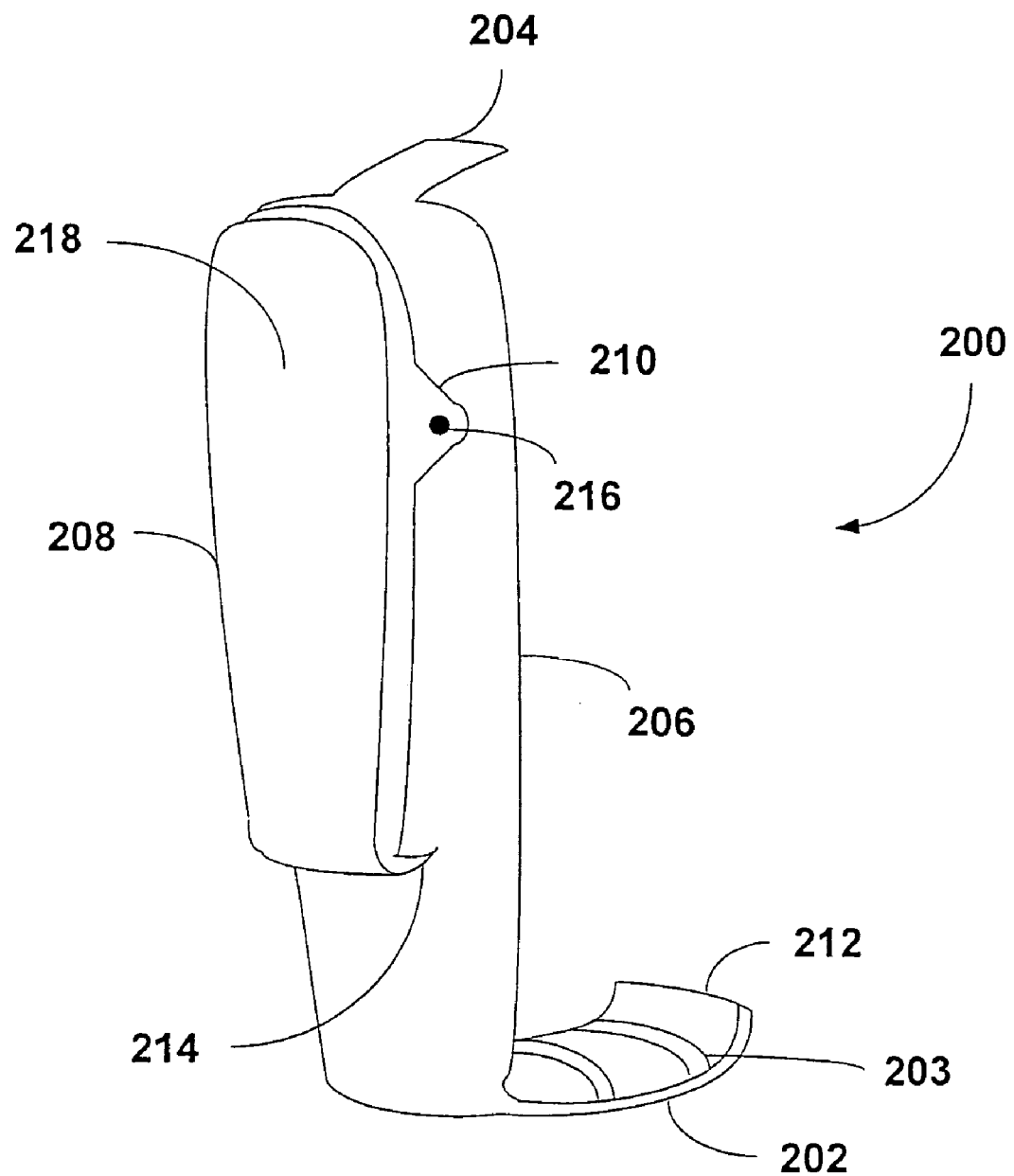
FIG. 9 shows a perspective view of a mounting clip according to an embodiment of the invention.

A mounting clip 200 according to another embodiment of the present invention is shown in FIG. 9. In FIG. 9, the mounting clip 200 includes, but is not limited to, a leg portion 206, a first foot 204 and a second foot 202. The first foot 204 and the second foot 202 may engage the housing of a personal device such as, but not limited to, personal medical devices, personal electronic devices, infusion devices, medical monitors and the like. The leg portion 206 may be sized such that the first foot 204 and the second foot 202 engage the housing of the personal device. The first foot 204 and the second foot 202 may engage the housing of a personal device such that the personal device is frictionally secured in between the first foot 204 and the second foot 202 and such that it rest up against the leg portion 206. According to another embodiment of the present invention, the first foot 204 may include a dovetail configuration such as the dovetail configuration 35 shown in FIG. 3C to provide a mechanical retention of the personal device.

The mounting clip 200 may also include, but is not limited to, a lever portion 208 and a hinge mechanism 210. The hinge mechanism 210 may be secured to the leg portion 206 via a hinge pin 216. The hinge pin 216 may be disposed within mounting elements (not shown) displaced on the leg portion 206 such that the lever portion 208 is rotatably secured against the leg portion 206. Moreover, the lever portion 208 may engage a spring element disposed adjacent the hinge mechanism 210 so that, by depressing the lever portion 208, the lever portion 208 may rotate about the hinge pin 216. As the lever portion 208 is rotated, a supporting item such as a strap, belt an undergarment or other article of clothing, for example, may be inserted between the lever portion 208 and the leg portion 206, thereby allowing a user of the personal device to maintain the personal device in a secure fashion on the user's body.

According an embodiment of the present invention, the first foot 204 may extend away from the leg portion 206 in a substantially perpendicular fashion. According to another embodiment of the present invention, the first leg 204 may slightly angle away from the leg portion 206. In addition, the first foot 204 may be somewhat elastic to allow a small amount of movement or "play," thereby allowing a user to maneuver the first foot 204 over the housing of a personal device.

Because the combination of the first foot 204 and the second foot 202 adequately secures the mounting clip 200 against the housing of a personal device, in some embodiments there is no need for the first foot 204 or the second foot 202 to include a locking mechanism or other securing device. However, according to other embodiments of the present invention, the first foot 204 may include a rotatable cam 82, for example, as shown in FIGS. 7A, 7B and 7C. In addition, according to embodiments of the present invention, the first foot 204 may also include a snap tab beam, such as the snap tab beam 68 shown in FIG. 6B, for example.

The second foot 202 may be sized such that the depth of a personal device fits within its boundaries. The second foot 202 may also include a lip 212 that angles toward the first foot 204. According to embodiments of the present invention, the lip 212 may extend up and around the perimeter of a personal device, thereby providing an additional mechanism for securing the personal device within the mounting clip 200. According to embodiments of the present invention, the second foot 202 may also include ridges 203 for providing a depression in which the personal device may rest or for providing a recess for various components of the personal device. For example, if the personal device includes a bottom "bumper," the bottom bumper of the personal device may rest in the recess formed by the ridges 203.

According to embodiments of the present invention, the lever portion 208 may include a tip 214 for providing additional frictional contact against a strap, a belt, an article of clothing or the like or for providing a return that mechanically wraps around a strap, a belt an article of clothing or the like. Moreover, the lever portion 208 may be designed to include a breakaway point 218. The breakaway point 218 may be intentionally designed as an area of the lever portion 208 that is structurally weaker than other areas of the lever portion 208. By including the breakaway point 218 on the lever portion 208, if sufficient force is exerted on the mounting clip 200 to cause an overload condition, the breakaway point 218 may allow the lever portion 208 to flex or even break, thereby directing the overloading forces away from the personal device.

The breakaway point 218 may be implemented in a variety of ways. For example, according to embodiments of the present invention, the breakaway point 218 may by implemented by providing an area of the lever portion 208 that is physically thinner than other areas of the lever portion 208 and, consequently, structurally weaker. According to other embodiments of the present invention, the lever portion 208 may be provided with a groove or cut-out area that is formed across or partially across an area of the lever portion 208 to provide a structurally weaker area of the lever portion 208. According to yet other embodiments of the present invention, the lever portion 208 may be provided with a hollow interior at the breakaway point 218 to provide a structurally weaker area of the lever portion 208.

The breakaway point 218 may be positioned in a variety of locations on the lever portion 208. For example, according to an embodiment of the present invention, the breakaway point 218 may be positioned on an area of the lever portion 208 that resides above the hinge mechanism 210. According to another embodiment of the present invention, the breakaway point 218 may be positioned in proximity to one of the ends of the lever portion 208.

According to embodiments of the present invention, other mechanisms may also be employed with the mounting clip 200 to mitigate the effects of overloading forces applied to the mounting clip 200. For example, a dovetail configuration such as the dovetail configuration 35 shown in FIG. 3C may be included with the first foot 204 or the second foot 202, or both, to mitigate the effects of overloading forces or other forces applied to the mounting clip 200.

According to embodiments of the present invention, the first foot 204, the leg portion 206 and the second foot 202 may be integrally formed. Also, the first foot 204, the leg portion 206 and the second foot 202 may be formed in an essentially "C-shaped" configuration.

Figure 10:
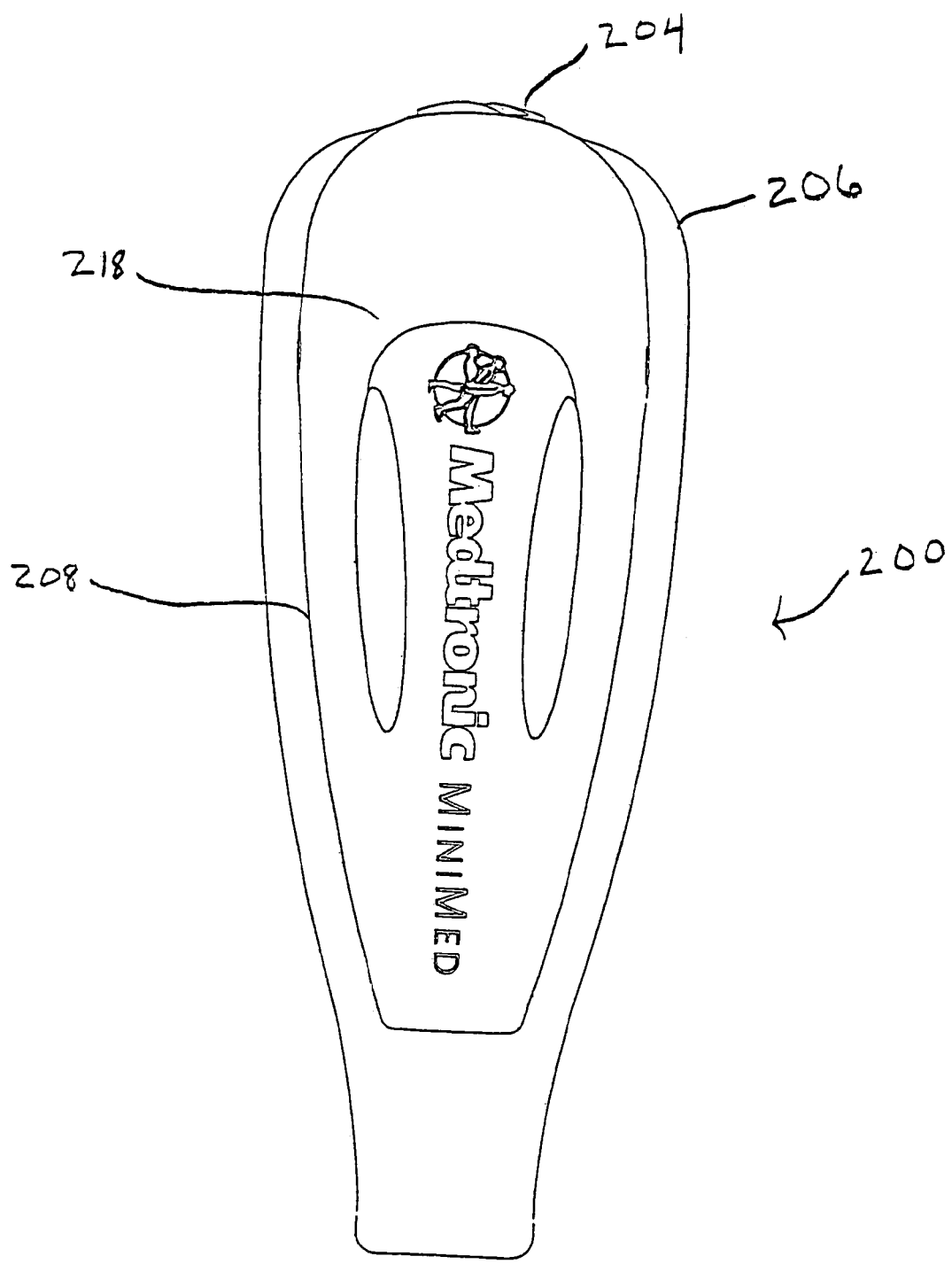
FIG. 10 shows a rear view of a mounting clip according to an embodiment of the invention.

FIG. 10 shows a rear view of the mounting clip 200. The view of the mounting clip 200 shown in FIG. 10 includes, but is not limited to, the leg portion 206, the first foot 204, the lever portion 208 and the breakaway point 218. According to embodiments of the present invention, the mounting clip 200 may be sized to accommodate a variety of personal devices and, thus, the mounting clip 200 may be made in a variety of sizes. In addition, the mounting clip 200 may also be designed with lines and angles that are comfortable in a user's hand and are also aesthetically pleasing.

Figure 11:
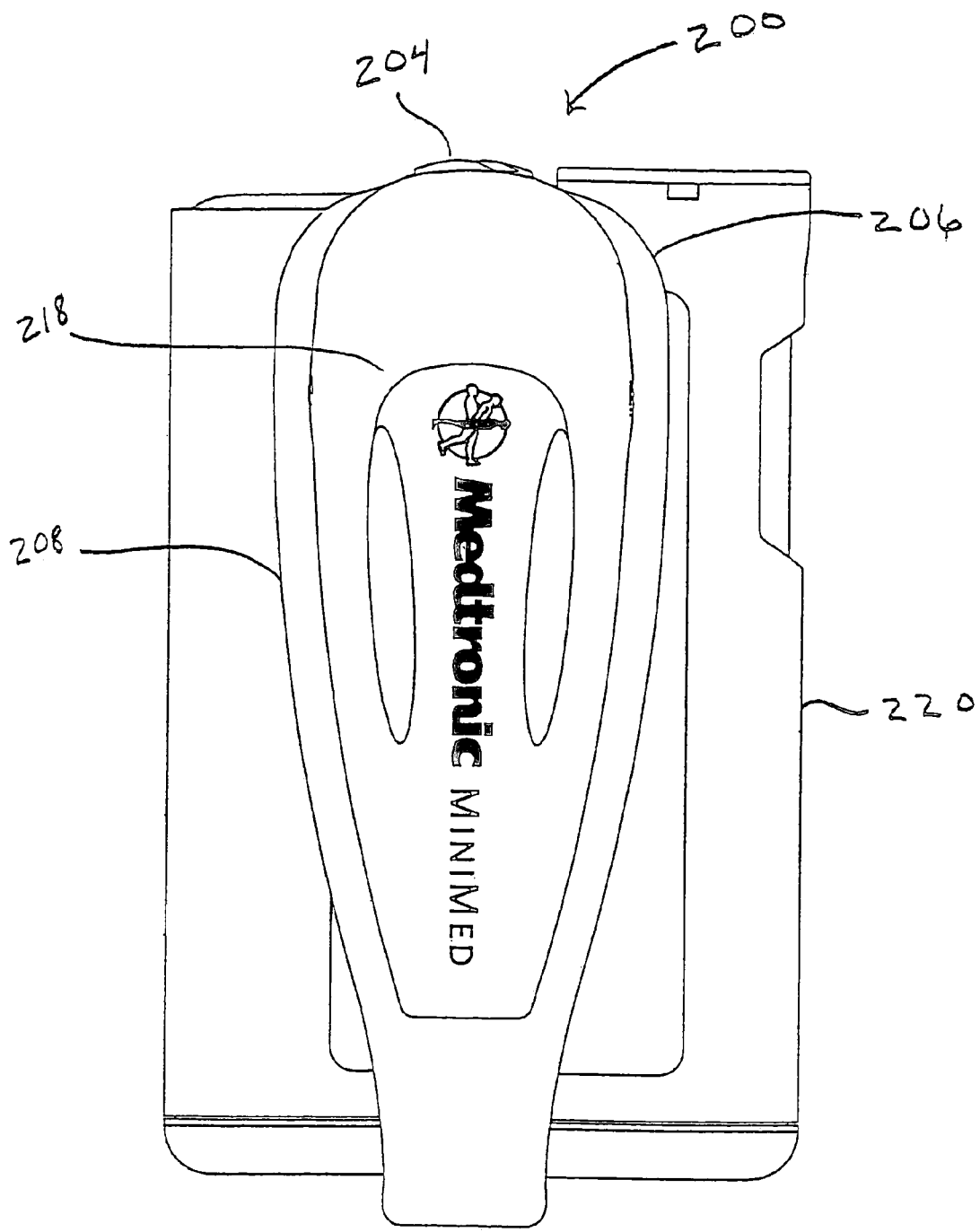
FIG. 11 shows a rear view of a mounting clip utilized with a personal device according to an embodiment of the invention.
Figure 12:
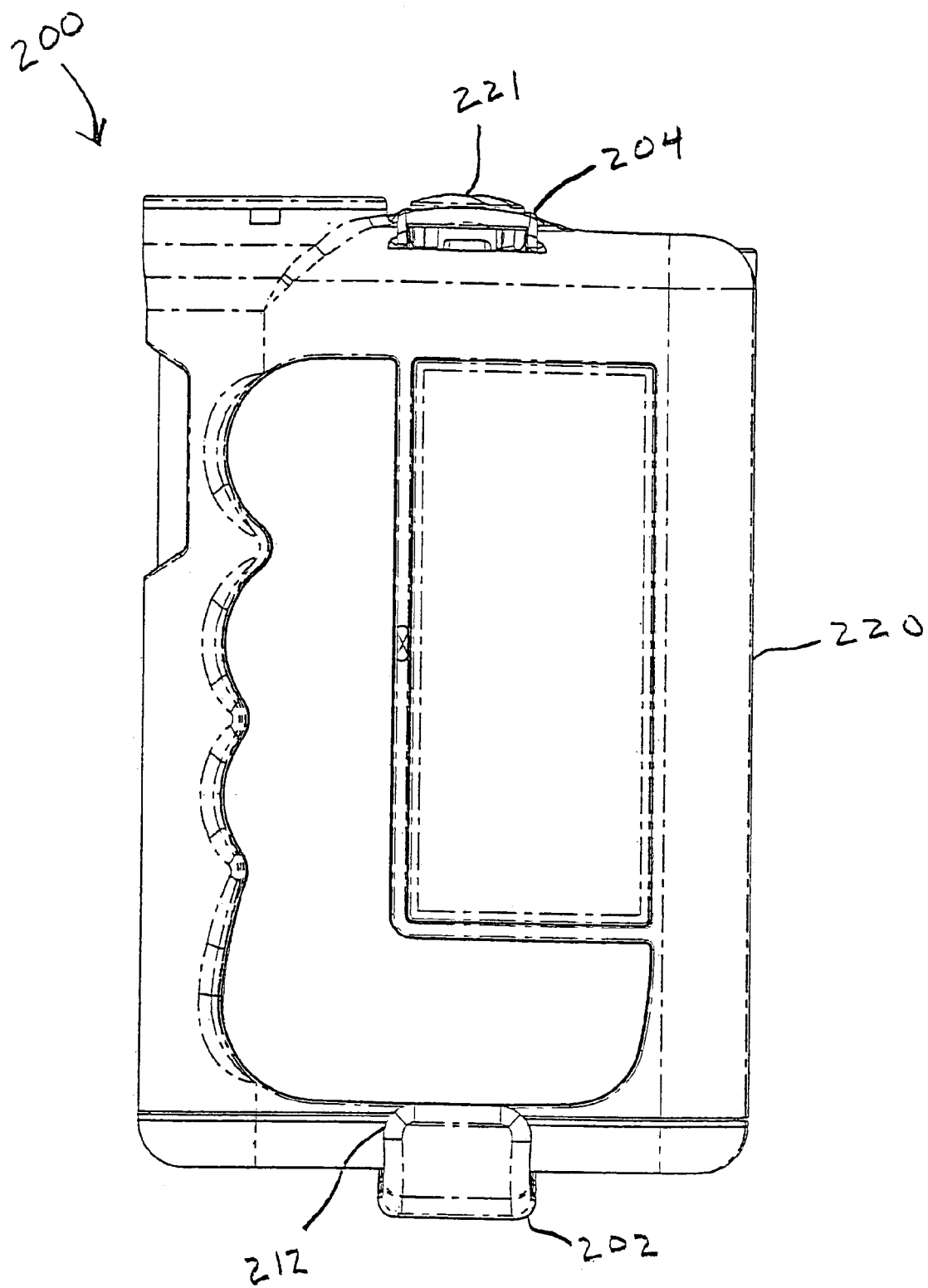
FIG. 12 shows a front view of a mounting clip utilized with a personal device according to an embodiment of the invention.

According to embodiments of the present invention, the lever portion 208 may include company names, logos or trademarks, such as "Medtronic MiniMed," for example. Also, the lever portion 208 may include cutouts that may be employed for stylistic, aesthetic or structural reasons. A rear view of the mounting clip 200 being utilized with a personal device 220 is shown in FIG. 11 while a front view of the mounting clip 200 being utilized with a personal device 220 is shown in FIG. 12.

Figure 13:
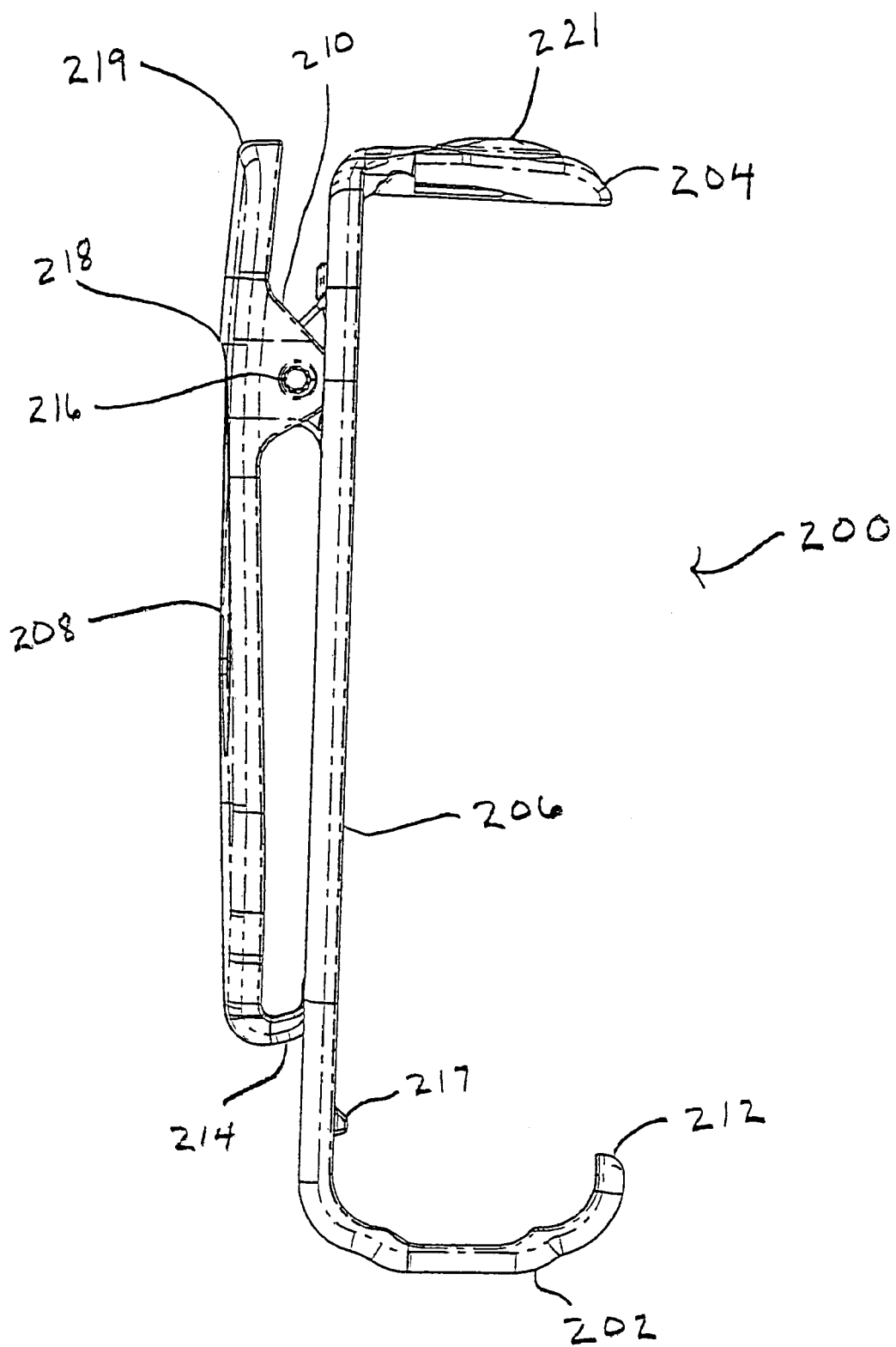
FIG. 13 shows a side view of a mounting clip according to an embodiment of the invention.
Figure 14:
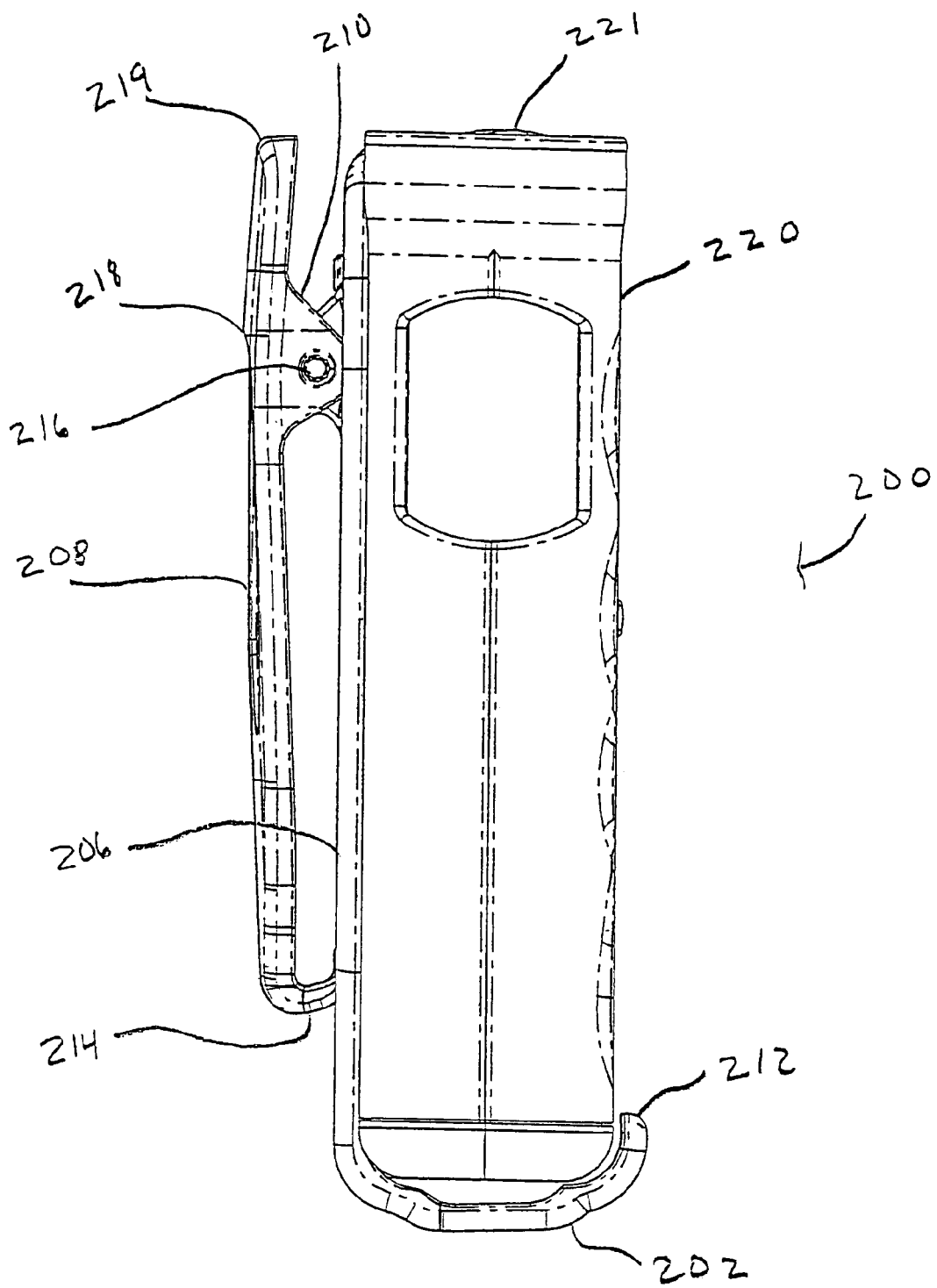
FIG. 14 shows a side view of a mounting clip utilized with a personal device according to an embodiment of the invention.

FIG. 13 shows a side view of a mounting clip 200 while FIG. 14 shows a side view of a mounting clip 200 in which a personal device 220 has been mounted according to an embodiment of the present invention. According to an embodiment of the present invention, in FIG. 14, the first foot 204 (not visible in FIG. 14) and the second foot 202 frictionally fit against a first portion and a second portion, respectively, of the personal device 220. Also, as can be seen in FIG. 14, the lip 212 extends up and around a face of the housing of the personal device and provides an extra measure of security for maintaining the position of the personal device 220.

As can also be seen in FIGS. 13 and 14, the lever portion 208 may be disposed against a hinge mechanism 210. The hinge mechanism 210 may be an integral part of the lever portion 208 or may be a separate part that is attached to the lever portion 208. The hinge mechanism 210 may rest against a spring (not shown) and is secured by a hinge pin 216.

According to embodiments of the present invention, as shown in FIG. 13, the leg portion 206 may include one or more tabs 217 which may be used in conjunction with grooves on a personal device for guiding the mounting clip 200 onto the personal device and/or for securing the personal device against the mounting clip 200. Also, in the embodiment of the invention in FIGS. 13 and 14, the mounting clip 200 may include a rotatable cam 221, which may be used to lock the personal device into place. The rotatable cam 221 may be similar or identical to the rotatable cam 82, for example, as shown in FIGS. 7A, 7B and 7C.

In FIGS. 13 and 14, according to embodiments of the present invention, by depressing a first end 219 of the lever portion 208, the lever portion 208 may rotate about the hinge pin 216, thereby creating a space underneath the hinge mechanism 210 and between the lever portion 208 and the leg portion 206 into which a supporting member such as, for example, a strap, a belt, an undergarment, another article of clothing or the like may be positioned or inserted. The lever portion 208 may also include a tip 214 that provides increased frictional resistance against the supporting member or that wraps around a supporting member.

According to embodiments of the present invention, the mounting clip 200 may be fabricated from a variety of materials. For example, the mounting clip 200 and its various components may be formed from any suitable materials such as, for example, plastics, thermoplastics, polycarbonate, polymers or the like, having suitable strength, durability and resiliency. According to other embodiments of the present invention, the mounting clip 200 and its various components may be formed from polycarbonate. For example, referring to FIG. 13, the leg portion 206 and the lever portion 208 may be made from, without limitation, a glass filled polycarbonate with carbon fiber added for strength and PTFE (TEFLON) added for lubricity. According to embodiments of the present invention, the percentage of PTFE added may be 10%. Also, according to embodiments of the present invention, the rotatable cam 221 may be made from a polycarbonate/ABS alloy with 10% PTFE for lubricity.

In addition, according to embodiments of the present invention, the mounting clip 200 may be fabricated in a variety of ways. For example, the mounting clip 200 and its various components may be formed by molding, stamping, machining, combinations or processes, or other suitable manufacturing processes.

FIG. 15 shows a method of utilizing a mounting clip according to an embodiment of the present invention. At step 230, the second end 202 of the mounting clip 200 may engage a second end of the personal device 220. Step 230 may be seen pictorially at position A in FIG. 16A. At step 232, the first end 204 of the mounting clip 200 may engage a first end of the personal device 220. Step 232 may be seen pictorially at position B in FIG. 16A. The direction of movement for the mounting clip 200 for steps 230 and 232 may be seen by the arrows C in FIG. 16A.

Figure 16B:
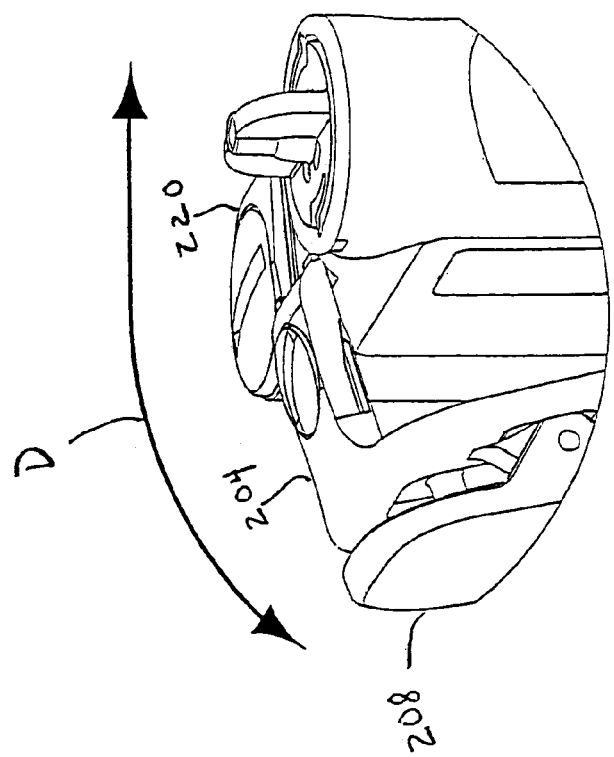
FIG. 16B shows pictorial representation of a method of a mounting clip with a personal device according to an embodiment of the invention.
Figure 16A:
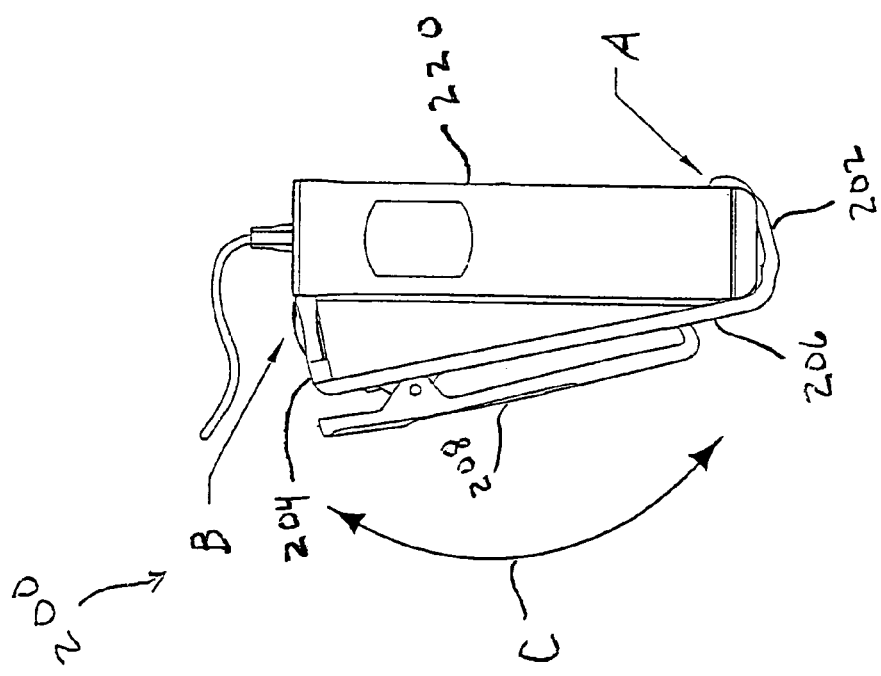
FIG. 16A shows pictorial representation of a method of a mounting clip with a personal device according to an embodiment of the invention.

After the first end 204 of the mounting clip 200 has engaged a first end of the personal device 220 in step 232, the mounting clip 200 may be secured around the personal device 220 at step 234. If the mounting clip 200 secures the personal device 220 via friction fit, the mounting clip 200 may be secure around the personal device 220 following engagement by the first end 204 of the mounting clip 200 of the first end of the personal device 220 at step 232. If the mounting clip 200 includes a rotatable cam or other locking mechanism, step 234 may include rotating the rotatable cam to lock the mounting clip 200 to the personal device 220 or may include performing another locking step with another locking mechanism to ensure that the mounting clip 200 is secure around the personal device 220. The mounting clip 200 may be removed from or positioned onto the personal device 220 by moving the mounting clip 200 in the direction of the arrows D as shown in FIG. 16B.

Once the mounting clip 200 has been secured onto the personal device 220, the mounting clip 200 and the personal device 220 may be attached to a supporting member using the lever portion 208. For example, the mounting clip 200 and the personal device 220 may be attached to a strap, a belt, an undergarment or some other article of clothing.

In preferred embodiments, the mounting clips described above are manufactured in an economical manner. According to one embodiment, the mounting clip is integrally formed as a one piece structure. In other embodiments, the mounting clip is assembled from two or more pieces that are formed separately. Such components may be formed from any suitable materials such as plastics, polymers, or the like, having suitable strength, durability and resiliency. Such components may be formed by molding, stamping, machining, combinations or processes, or other suitable manufacturing processes.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A mounting clip for removably attaching a personal device on a supporting member, comprising:
    a first foot for frictionally attaching the mounting clip to a first portion of the personal device;
    a second foot for frictionally attaching the mounting clip to a second portion of the personal device;
    a leg portion for connecting the first foot and the second foot; and
    a lever hingedly attached to the leg portion;
    wherein the lever rotates relative to the leg portion for positioning the supporting member between the lever and the leg portion;
    wherein the first foot includes a dovetail configuration for slide-on attachment and slide-off removal of the personal device, the dovetail configuration having a cascading facet configuration, and wherein the first foot has a locking mechanism for securing the clip to the personal device.

2. The mounting clip of claim 1, wherein the cascading facet configuration includes a plurality of outwardly and downwardly sloping facets for engaging corresponding surfaces on the personal device.

3. The mounting clip of claim 1, wherein the cascading facet configuration includes three outwardly and downwardly sloping facets for engaging corresponding surfaces on the personal device.

4. The mounting clip of claim 2, wherein the plurality of outwardly and downwardly sloping facets have different sloping angles relative to each other.

5. The mounting clip of claim 2, wherein the plurality of outwardly and downwardly sloping facets, when fully engaged to the personal device and subjected to an overload condition, elastically deform, slide from facet to facet along the corresponding surfaces of the personal device and separate from the personal device with reduced damage.

6. The mounting clip of claim 1, wherein the first foot includes channels formed thereon for providing inward flexibility to the first foot.

7. The mounting clip of claim 6, wherein the channels extend lengthwise on the first foot in the direction of engagement with the personal device.

8. The mounting clip of claim 1, wherein the first foot includes engagement stops for abutting against corresponding surfaces of the personal device.

9. The mounting clip of claim 1, wherein the locking mechanism includes a snap tab beam locking mechanism having a barb for interlocking with a bump provided on the personal device for locking the mounting clip to the personal device.

10. The mounting clip of claim 9, wherein the barb interlocks with a bump provided on a housing of the personal device.

11. The mounting clip of claim 9, wherein the snap tab beam locking mechanism is integrally formed with the foot portion.

12. A mounting clip for removably attaching a personal device on a supporting member, comprising:
    a first foot for frictionally attaching the mounting clip to a first portion of the personal device;
    a second foot for frictionally attaching the mounting clip to a second portion of the personal device;
    a leg portion for connecting the first foot and the second foot; and
    a lever hingedly attached to the leg portion;
    wherein the lever rotates relative to the leg portion for positioning the supporting member between the lever and the leg portion; and
    wherein the first foot includes a rotatable cam locking mechanism having one or more radial snap tabs having engagement elements for engaging corresponding surfaces on the mounting clip.

13. The mounting clip of claim 12, wherein the rotatable cam locking mechanism is formed separately from the first foot portion and subsequently attached to the first foot.

14. The mounting clip of claim 13, wherein the first foot is formed to include an opening shaped and sized for receiving the rotatable cam locking mechanism.

15. A personal device for attachment to a supporting member, comprising:
    a device housing including first engagement elements for receiving a mounting clip, the mounting clip including:
        a first foot for frictionally attaching the mounting clip to a first portion of the personal device;
        a second foot for frictionally attaching the mounting clip to a second portion of the personal device;
        a leg portion for connecting the first foot and the second foot; and
        a lever hingedly attached to the leg portion;
        wherein the lever rotates relative to the leg portion for positioning the supporting member between the lever and the leg portion;
        wherein the first foot includes a dovetail configuration for slide-on attachment and slide-off removal of the personal device, the dovetail configuration having a cascading facet configuration and wherein the first foot has a locking mechanism for securing the clip to the personal device.

16. The personal device of claim 15, wherein the cascading facet configuration includes a plurality of outwardly and downwardly sloping facets for engaging corresponding surfaces on the personal device.

17. The personal device of claim 15, wherein the cascading facet configuration includes three outwardly and downwardly sloping facets for engaging corresponding surfaces on the personal device.

18. The personal device of claim 16, wherein the plurality of outwardly and downwardly sloping facets have different sloping angles relative to each other.

19. The personal device of claim 16, wherein the plurality of outwardly and downwardly sloping facets, when fully engaged to the personal device and subjected to an overload condition, elastically deform, slide from facet to facet along the corresponding surfaces of the personal device and separate from the personal device with reduced damage.

20. A personal device for attachment to a supporting member, comprising:

a device housing including first engagement elements for receiving a mounting clip, the mounting clip including:

a first foot for frictionally attaching the mounting clip to a first portion of the personal device;

a second foot for frictionally attaching the mounting clip to a second portion of the personal device;

a leg portion for connecting the first foot and the second foot; and a lever hingedly attached to the leg portion;

wherein the lever rotates relative to the leg portion for positioning the supporting member between the lever and the leg portion; and wherein the first foot includes a rotatable cam locking mechanism having one or more radial snap tabs having engagement elements for engaging corresponding surfaces on the mounting clip.

21. The personal device of claim 20, wherein the rotatable cam locking mechanism is formed separately from the first foot and subsequently attached to the first foot.

22. The personal device of claim 21, wherein the first foot is formed to include an opening shaped and sized for receiving the rotatable cam locking mechanism.

* * * * *